(12) United States Patent
Sharrock

(10) Patent No.: US 6,994,675 B2
(45) Date of Patent: Feb. 7, 2006

(54) NON-INVASIVE MEASUREMENT OF SUPRASYSTOLIC SIGNALS

(76) Inventor: Nigel E. Sharrock, 625 E. 86th St., New York, NY (US) 10028

( * ) Notice: Subject to any disclaimer, the term of this patent is extended or adjusted under 35 U.S.C. 154(b) by 258 days.

(21) Appl. No.: 10/221,530

(22) PCT Filed: Jul. 19, 2001

(86) PCT No.: PCT/US01/22689

§ 371 (c)(1), (2), (4) Date: Sep. 13, 2002

(87) PCT Pub. No.: WO02/05726

PCT Pub. Date: Jan. 24, 2002

(65) Prior Publication Data

US 2003/0040675 A1     Feb. 27, 2003

Related U.S. Application Data

(60) Provisional application No. 60/219,790, filed on Jul. 19, 2000.

(51) Int. Cl.
*A61B 5/02*     (2006.01)

(52) U.S. Cl. ............... 600/500; 600/495; 600/490; 600/504; 600/547

(58) Field of Classification Search ........... 600/481, 600/485, 490–496, 500–503, 547

See application file for complete search history.

(56) References Cited

U.S. PATENT DOCUMENTS

| | | | | |
|---|---|---|---|---|
| 5,241,963 A | * | 9/1993 | Shankar | 600/481 |
| 5,343,867 A | | 9/1994 | Shankar | |
| 5,417,220 A | * | 5/1995 | Apple | 600/500 |
| 5,836,884 A | | 11/1998 | Chio | |
| 5,913,826 A | | 6/1999 | Blank | |
| 6,165,130 A | * | 12/2000 | Chio | 600/485 |
| 6,267,728 B1 | | 7/2001 | Hayden | |
| 6,309,359 B1 | | 10/2001 | Whitt et al. | |

* cited by examiner

*Primary Examiner*—Robert L. Nasser
*Assistant Examiner*—Navin Natnithithadha
(74) *Attorney, Agent, or Firm*—Milde & Hoffberg LLP

(57) ABSTRACT

An apparatus for assessing cardiovascular status of a mammal comprises a system for locally applying a pressure to an artery capable of restricting blood flow through said artery, a wideband external pulse transducer having an output and situated to measure suprasystolic signals proximate to said artery, and a computing device receiving said output for calculating vascular compliance values. The method described is particularly useful for determining cardiac output, assessing whether a pregnant female has preeclampsia or a patient has cardiac insufficiency, or assessing cardiac arrhythmias.

54 Claims, 23 Drawing Sheets

Typical signal from piezoelectric sensor

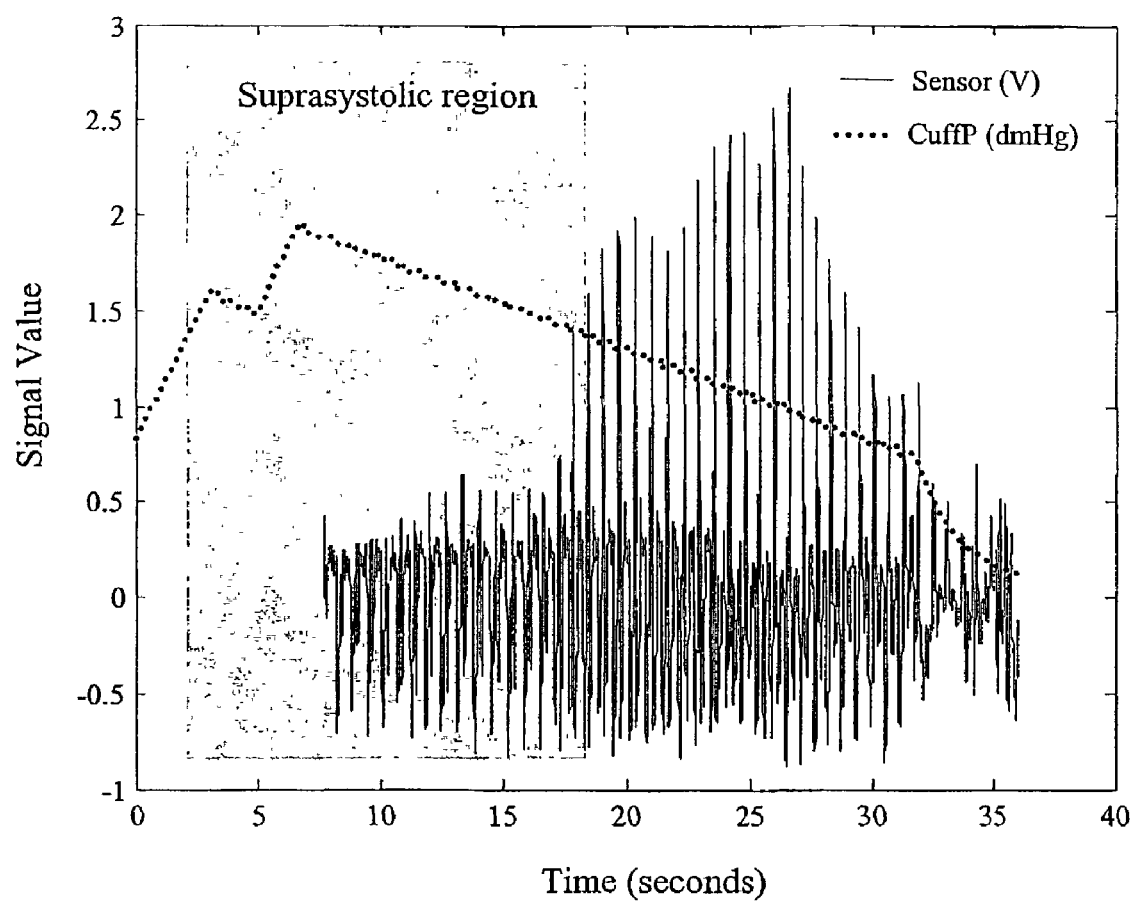
Figure 1: Typical signal from piezoelectric sensor

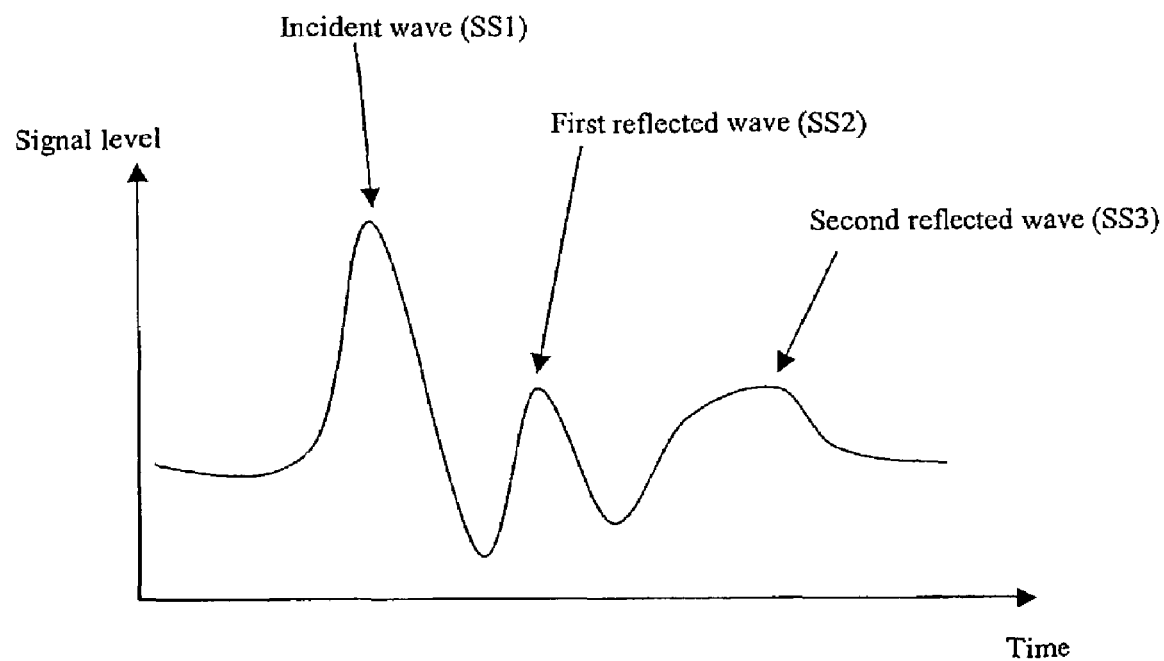
Figure 2: Idealised Suprasystolic Signal

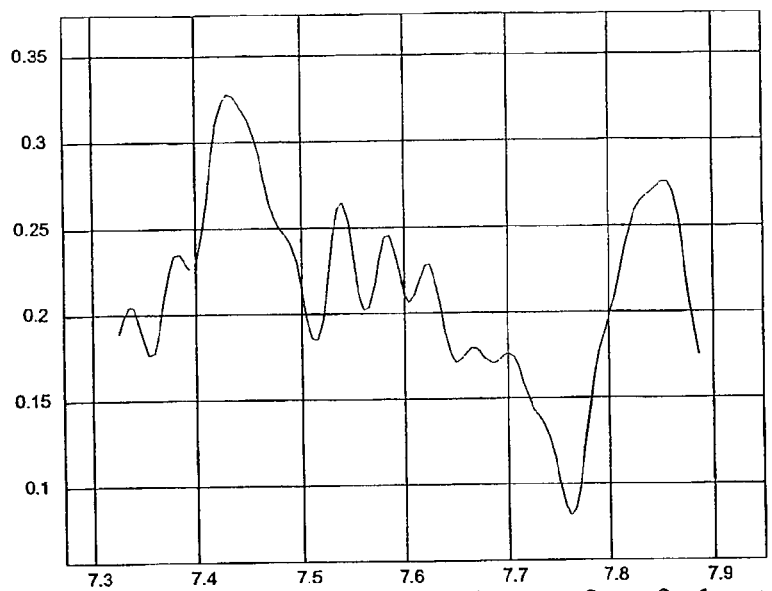
Figure 3: Suprasystolic waveform for heart failure patient.

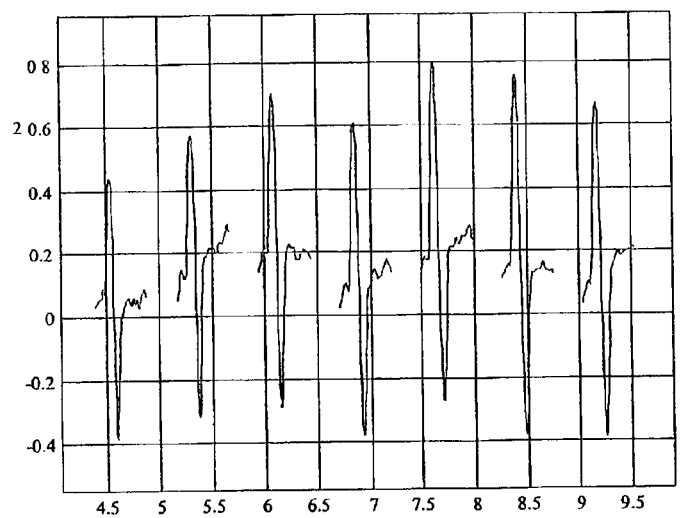
- SS1-2 = 33
- SS1-3 = 15.5
- dt1-2 = 0.20
- dV1 = 0.26
- dt1 = 0.035
- dV3 = 0.03
- Heart Rate = 87
- Compliance = 2.29
- BP = 125/65
- SV = 137
- CO = 12.0
Figure 4: Suprasystolic beats during anesthesia with a patient on a ventilator.

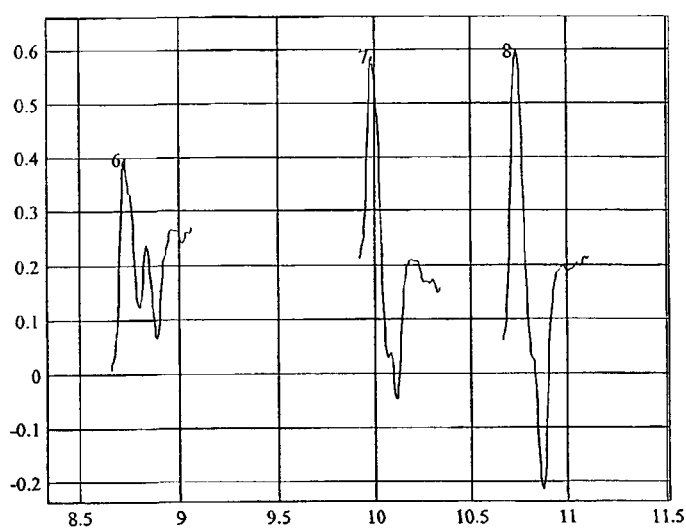
Figure 5: Patient in shock. Beats marked 7 and 8 are with the ventilator.
Values of beat #6
- SS1-2 = 1.65
- SS1-3 = 1.52
- dt1-2 = 0.12
- dV1 = 0.22
- dt1 = 0.03
- dV3 = 0.11
- Heart Rate = 89
- Compliance = 1.17
- BP = 75/55
- SV = 24
- CO = 1.17

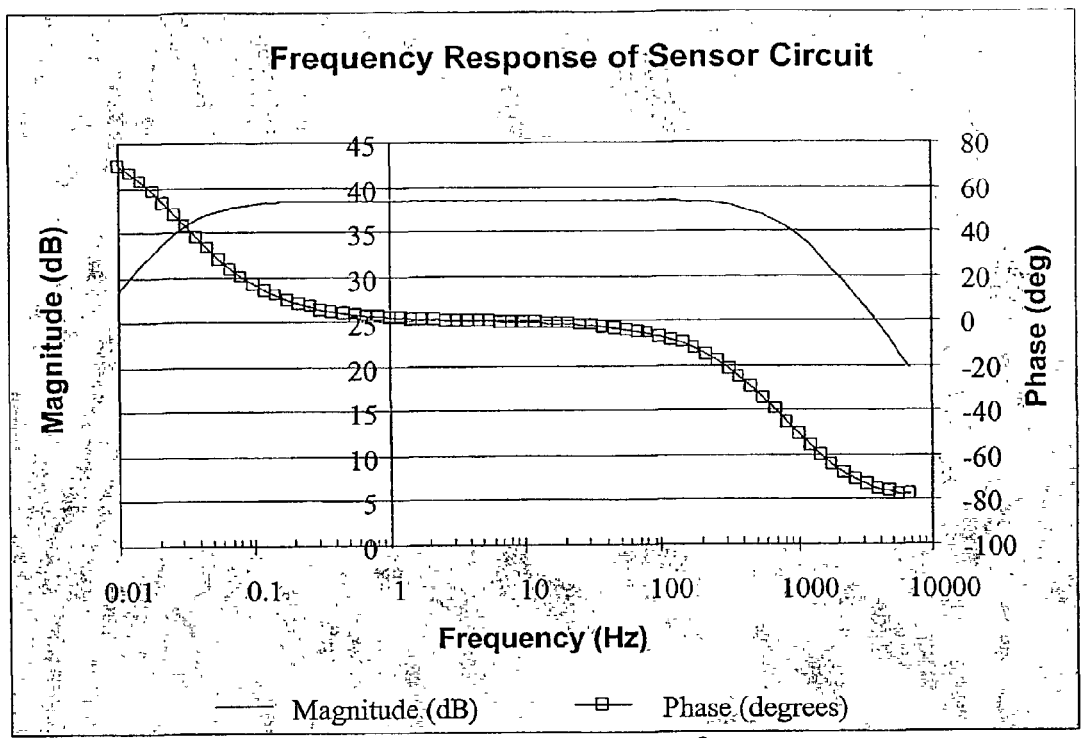
Figure 6: Frequency response of sensor

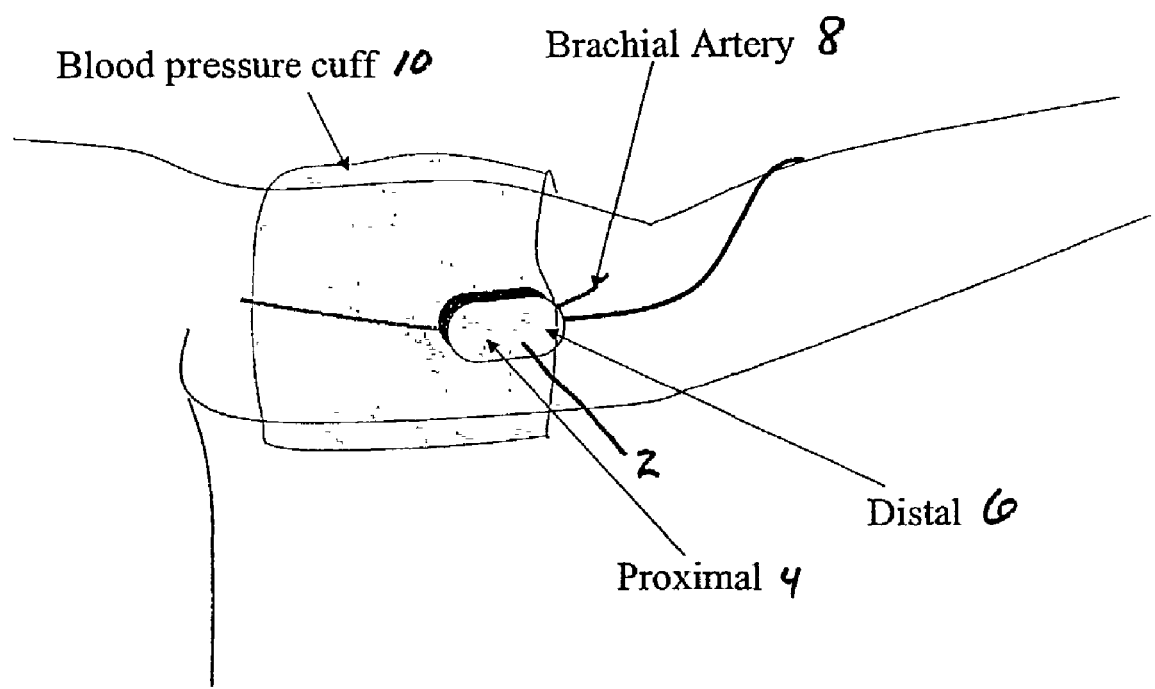
Figure 7: Placement of sensor

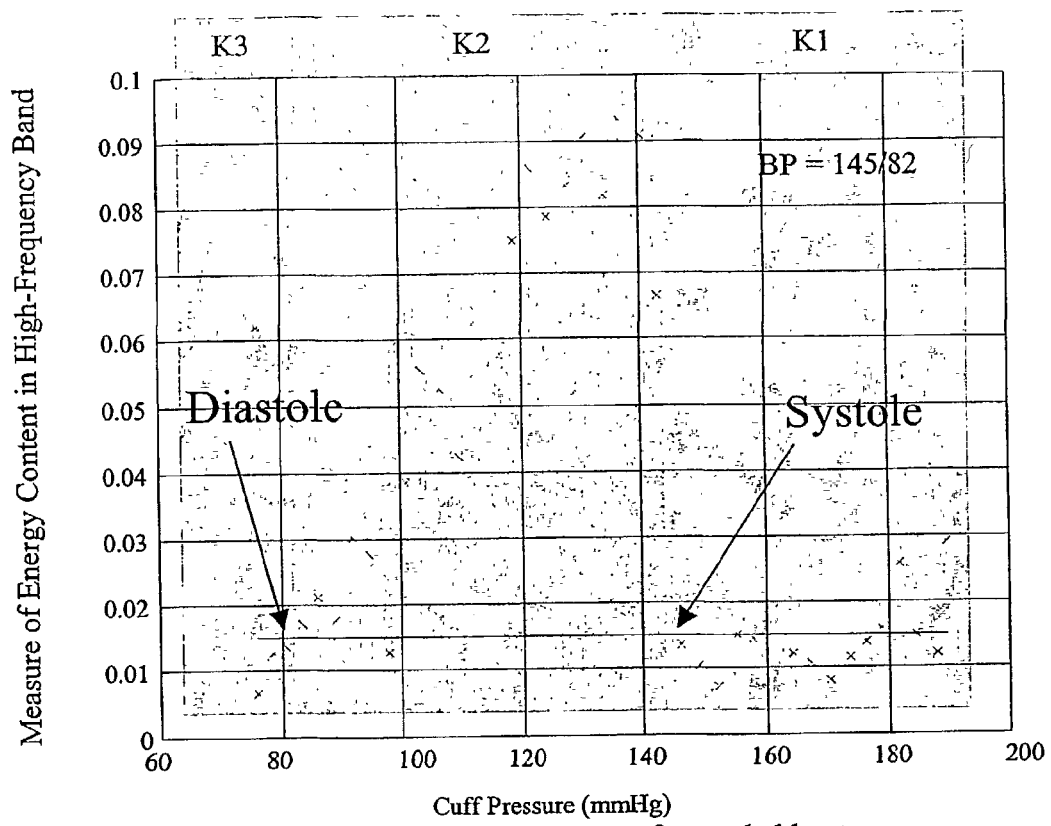
Figure 8: High frequency content of recorded beats

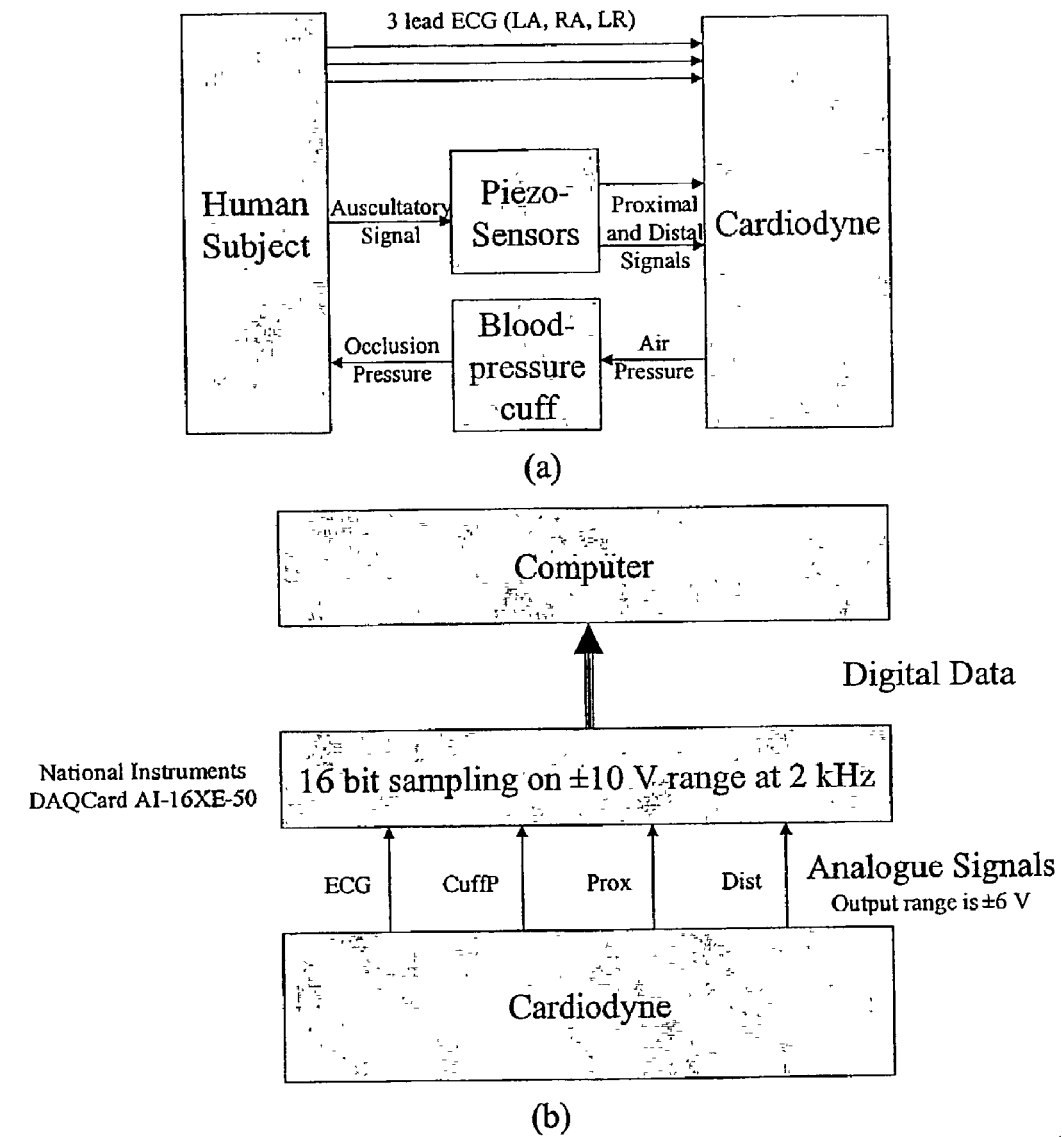
Figure 9: Measurement device interface with subject (a) and computer (b)

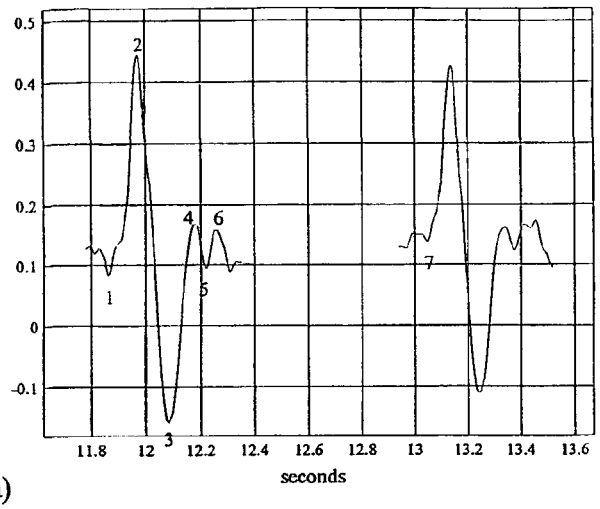

- SS1-2 = 8.3
- SS1-3 = 10.1
- dt1-2 = 0.21
- dV1 = 0.3
- dt1 = 0.06
- dV3 = 0.01
- Systole = 0.31
- Diastole = 0.83
- Heart Rate = 53
- Compliance = 1.86
- BP = 90/50
- SV = 74
- CO = 3.9

(a)

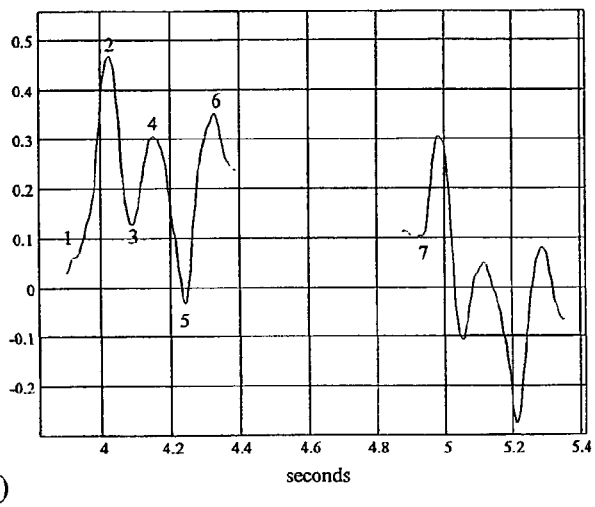

- SS1-2 = 1.01
- SS1-3 = 0.89
- dt1-2 = 0.13
- dV1 = 0.33
- dt1 = 0.05
- dV3 = 0.21
- Systole = 0.27
- Diastole = 0.70
- Heart Rate = 62
- Compliance = 1.01
- BP = 130/60
- SV = 70
- CO = 4.4

(b)

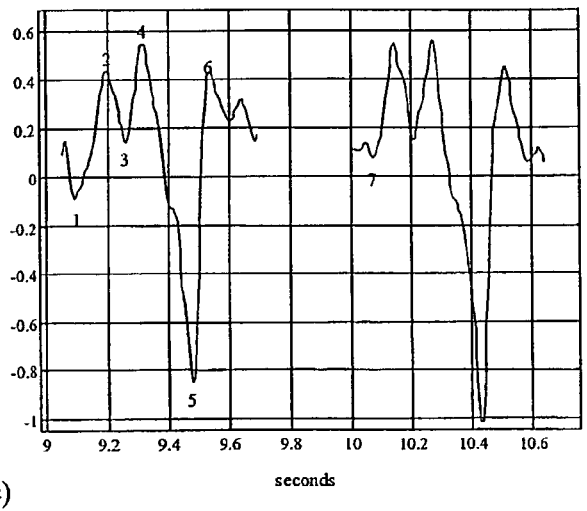

- SS1-2 = 0.28
- SS1-3 = 0.32
- dt1-2 = 0.12
- dV1 = 0.5
- dt1 = 0.11
- dV3 = 0.51
- Systole = 0.38
- Diastole = 0.60
- Heart Rate = 60
- Compliance = 0.67
- BP = 160/85
- SV = 50
- CO = 3.1

(c)

Figure 10: Representative suprasystolic waveforms for (a) young person, (b) moderately reduced compliance, (c) elderly person with hypertension. Vertical axis in all cases is in Volts.

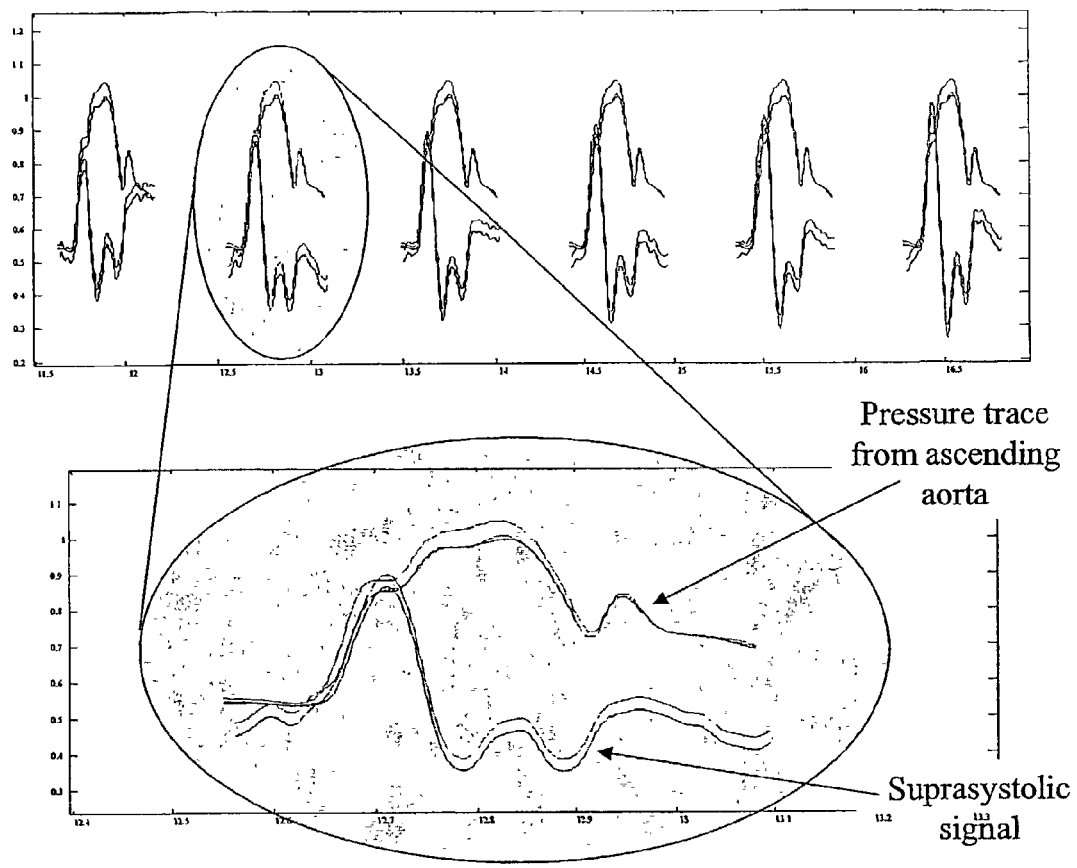
Figure 11: Correlation between suprasystolic signal and ascending aorta pressure

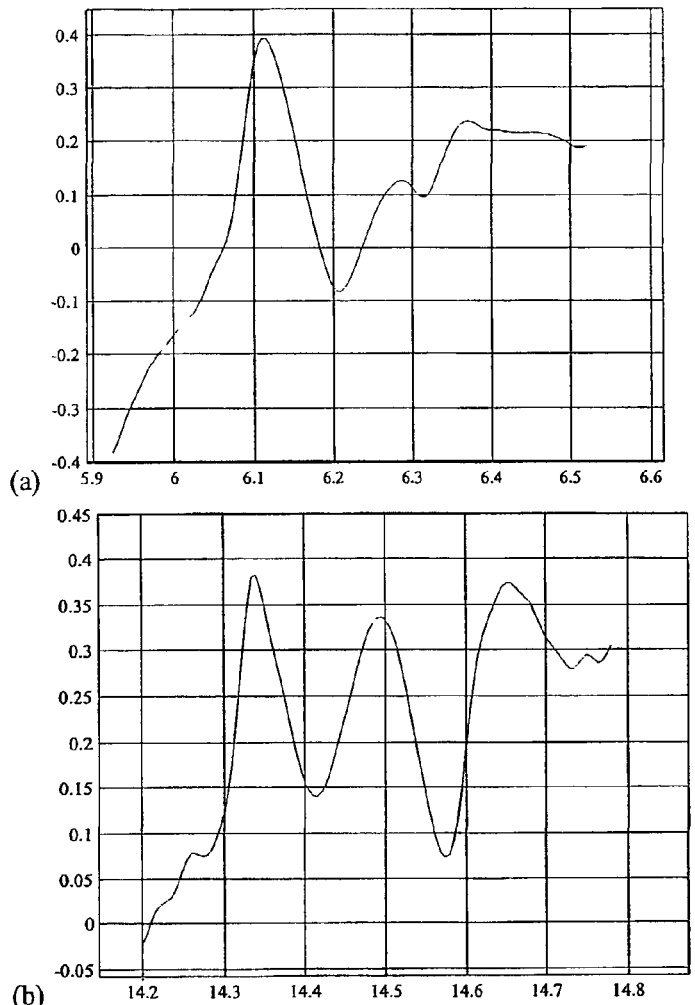
Figure 12: Suprasystolic waveforms for matched pregnant woman (a) without preeclampsia (b) with preeclampsia.

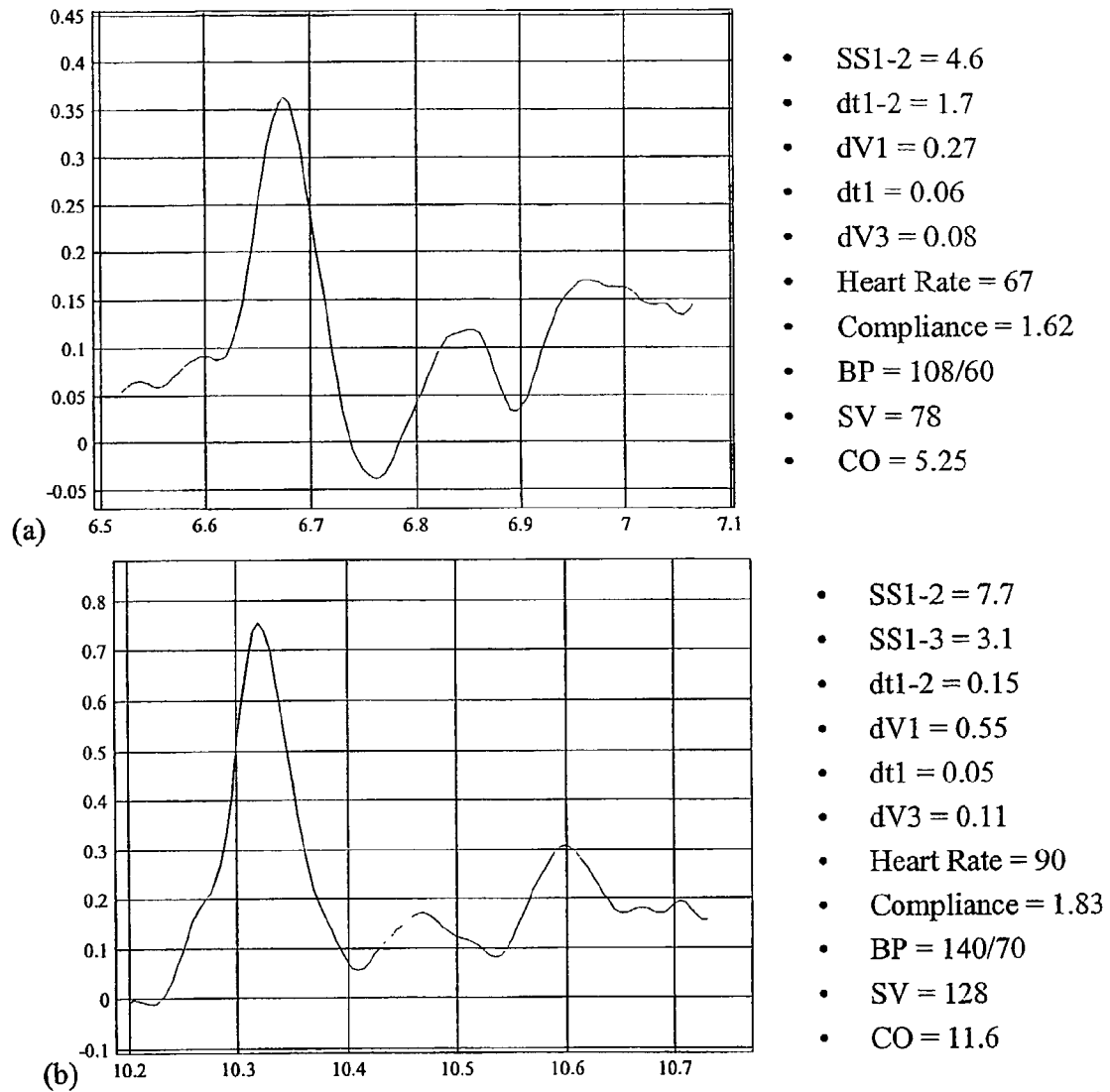
Figure 13: Suprasystolic waveform of subject (a) before and (b) after mild exercise.

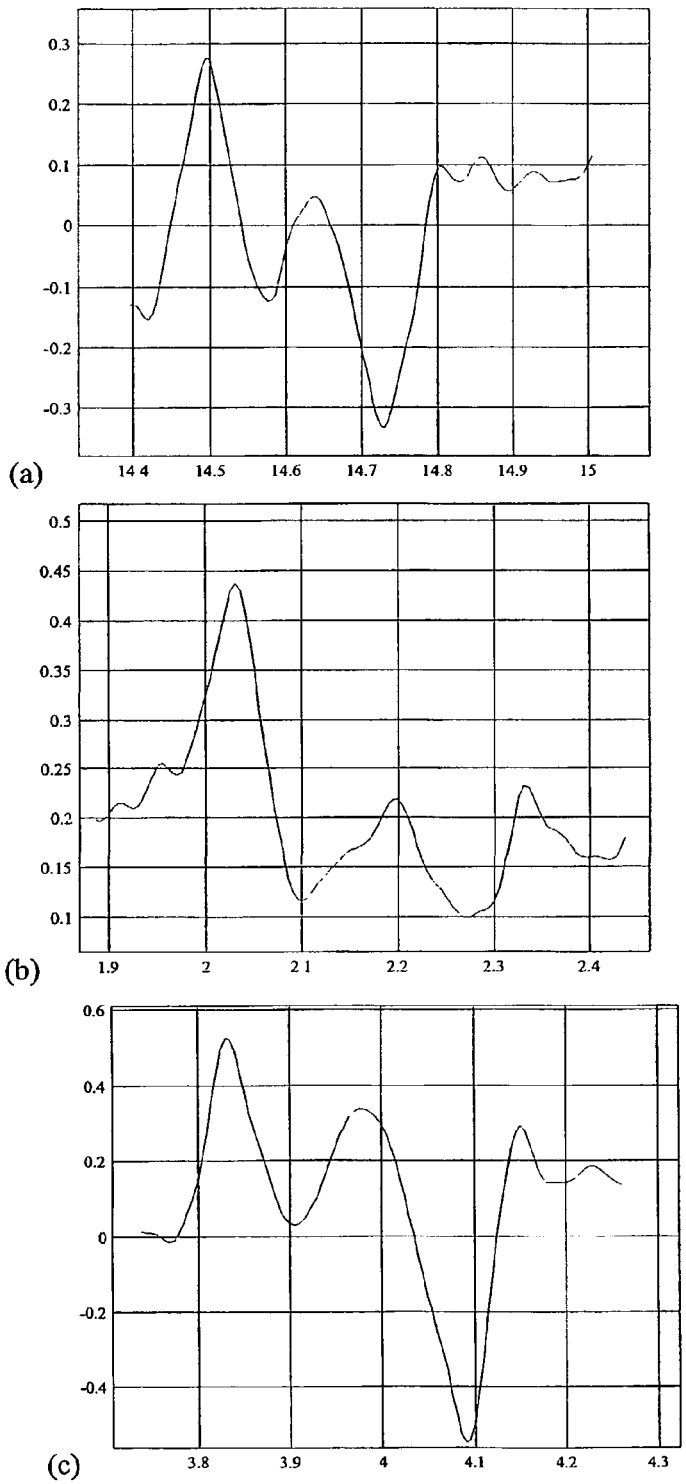
Figure 14: Waveforms during spinal anaesthesia (a) initially, (b) after extensive spinal and (c) after administration of ephedrine.

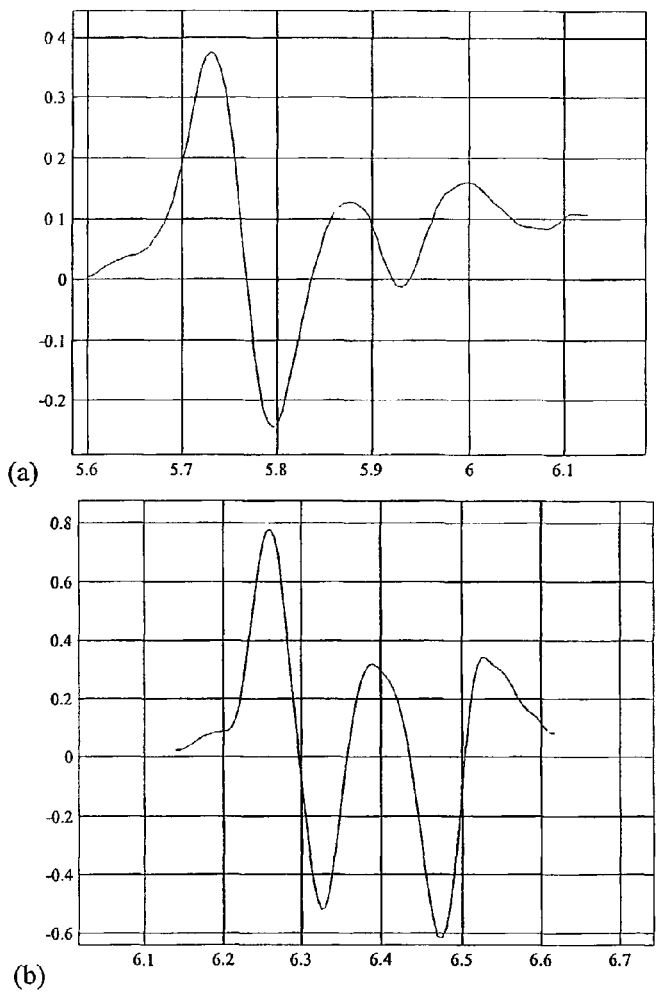
Figure 15: Waveform morphology after (b) the Cold Pressor test compared to prior measurements (a).

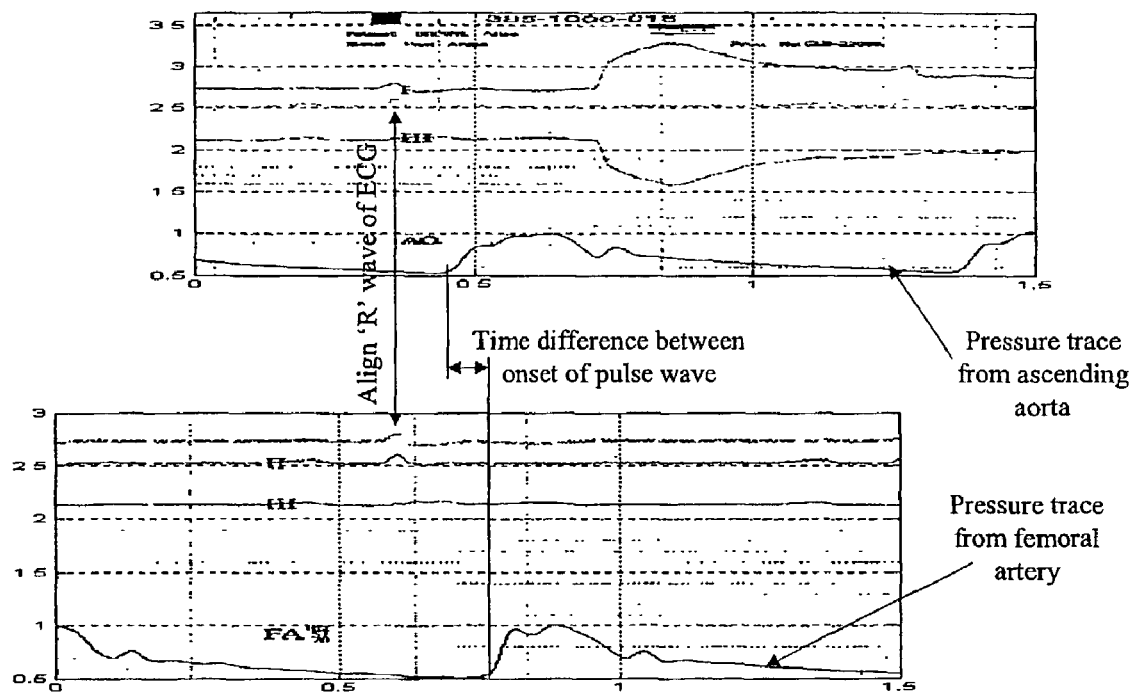
Figure 16: Determination of PWV from invasive pressure tracings.

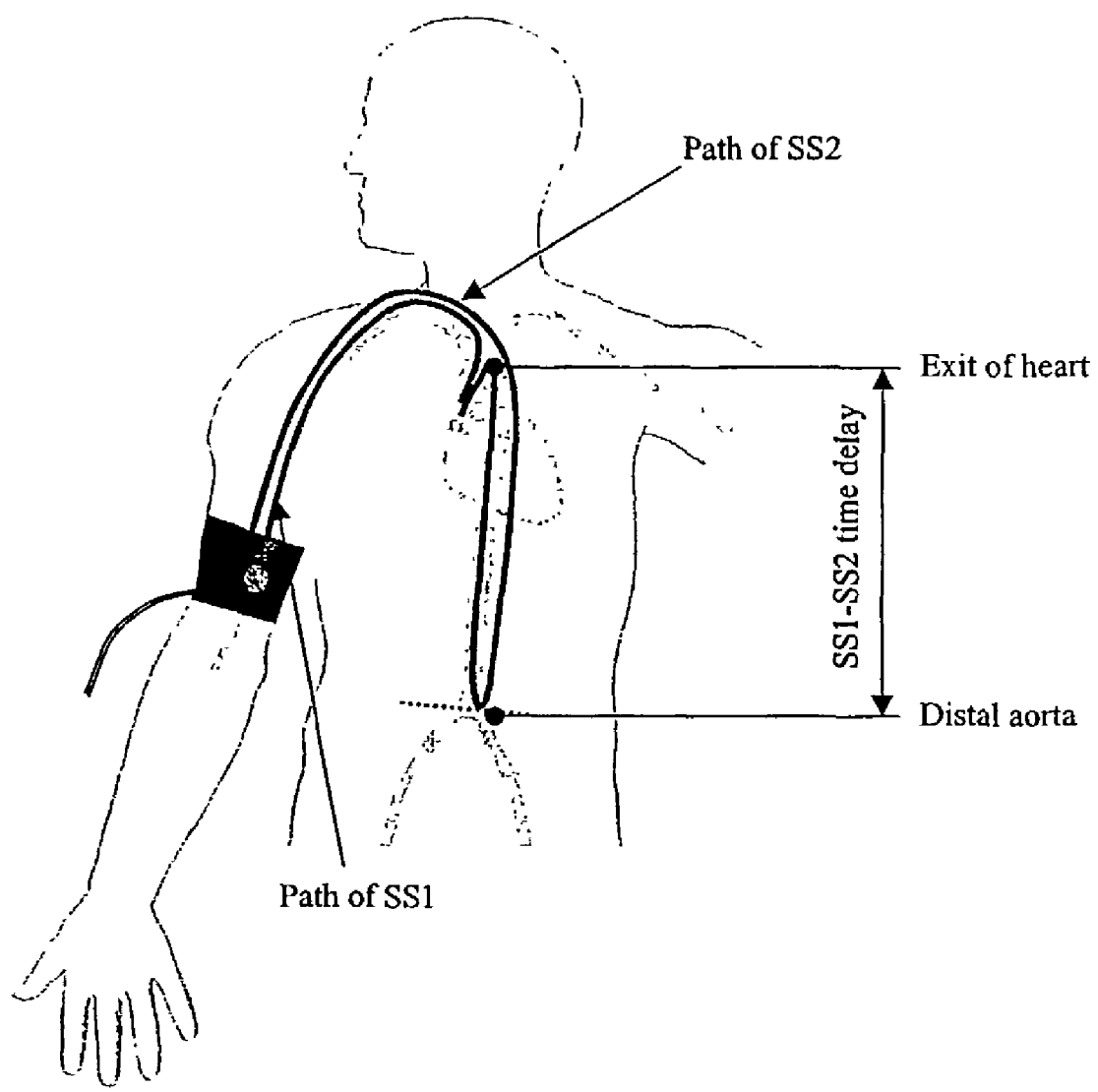
Figure 17: Suprasystolic pulse wave transit paths

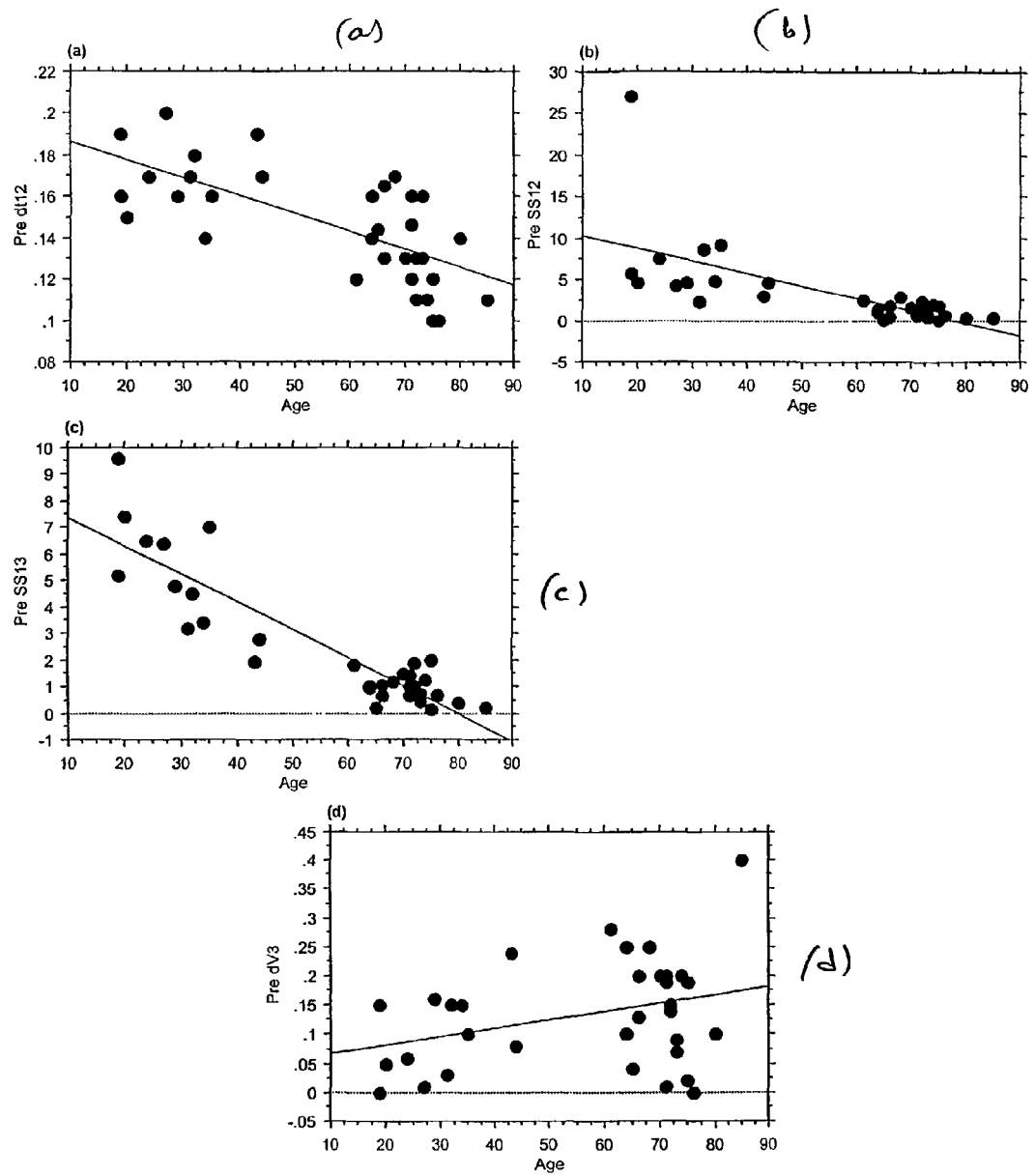
Figure 18: Regression of suprasystolic parameters against age

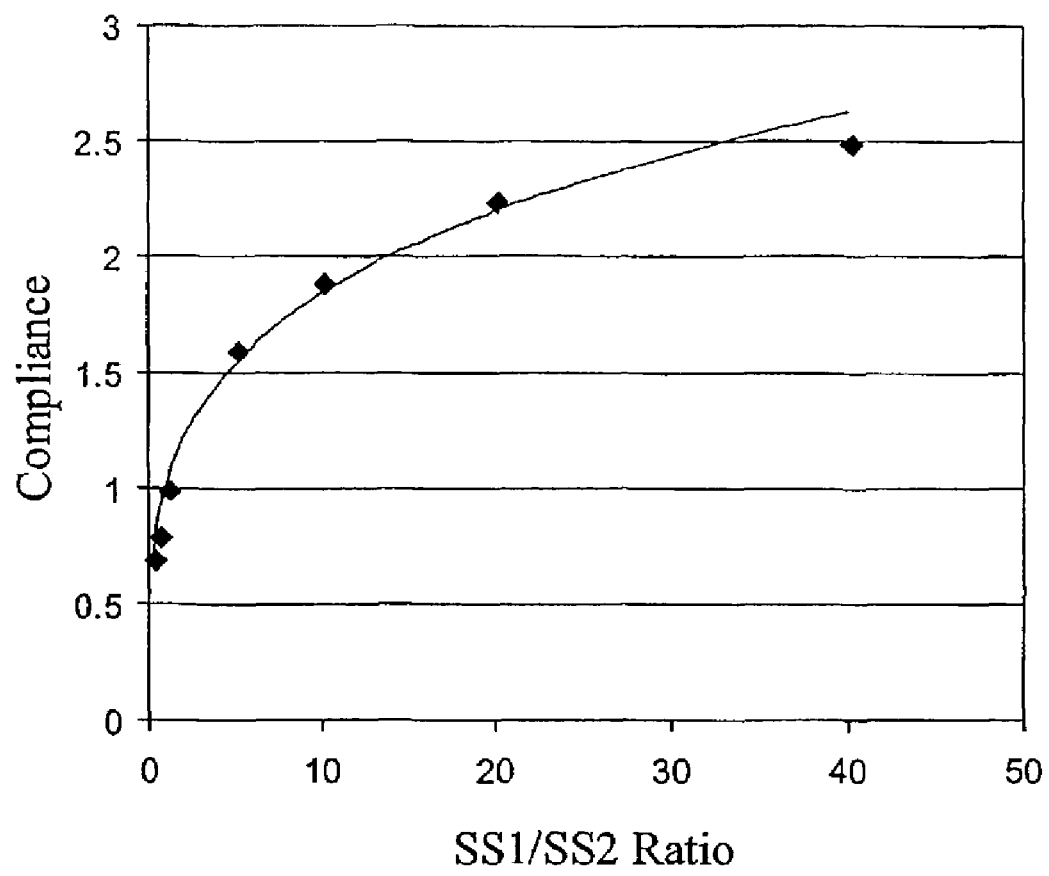
Figure 19: Relationship between SS1/SS2 and compliance.

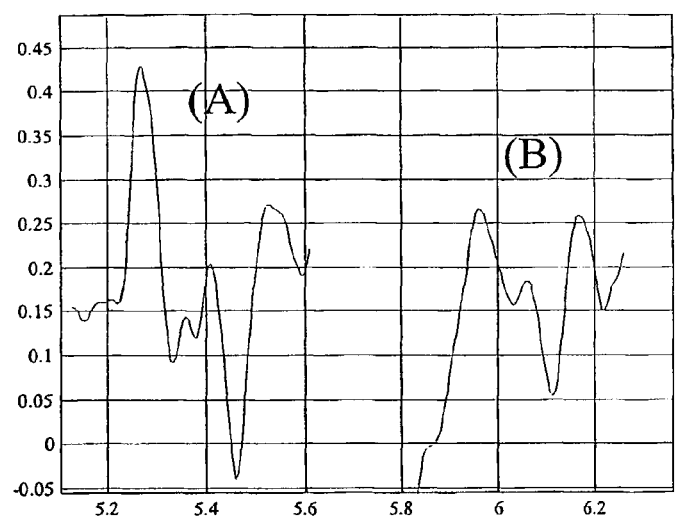
Figure 20: Example of arrhythmia in a suprasystolic waveform. Beat (A) is normal. Beat (B) is ectopic.

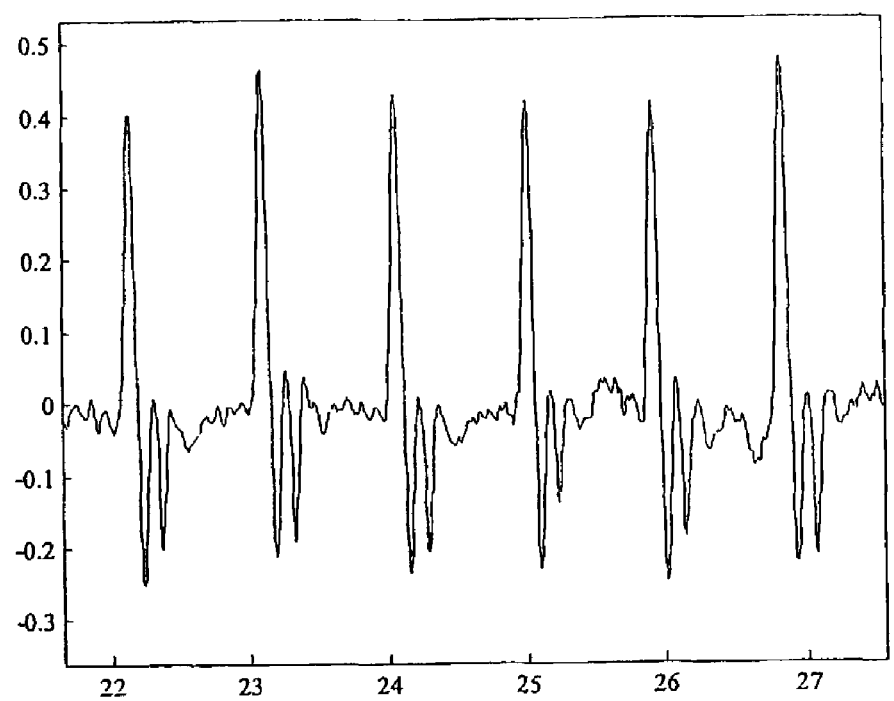
Figure 21: Effect of normal respiration on suprasystolic waveforms.

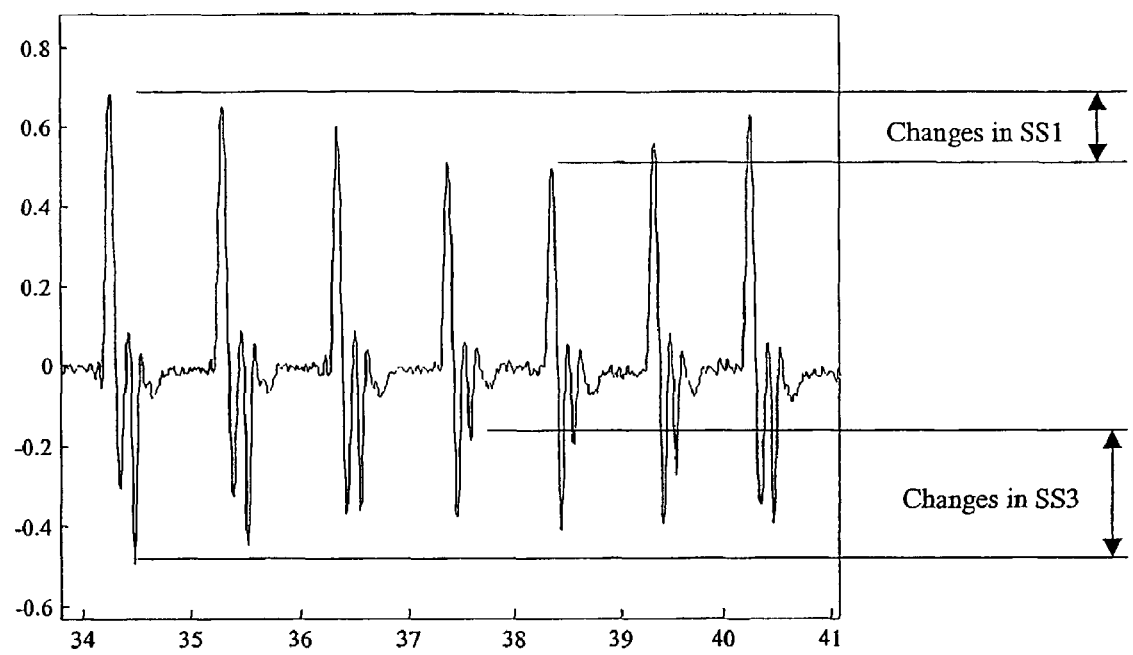
Figure 22: Changes in suprasystolic signal due to labored breathing.

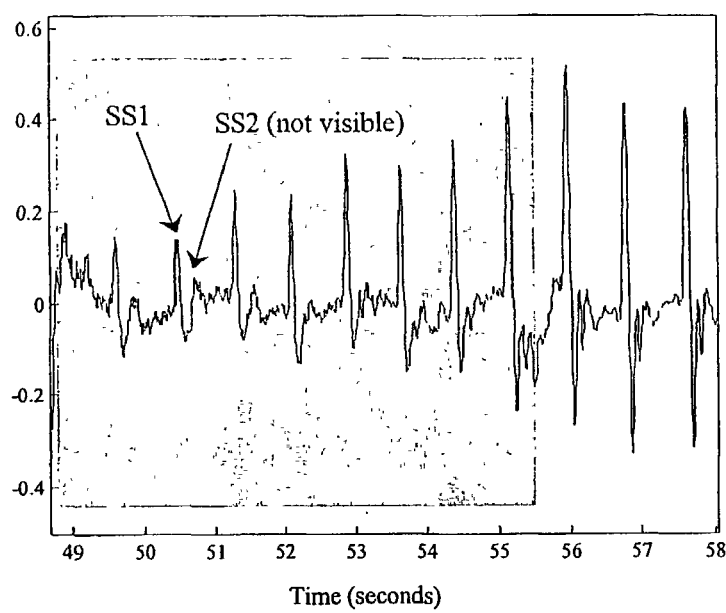
Figure 23: Suprasystolic waveform during Valsalva Maneuver. The shaded region indicates beats affected by the maneuver.

NON-INVASIVE MEASUREMENT OF SUPRASYSTOLIC SIGNALS

This application claims the benefit of Provisional Application No. 60/219,790, filed Jul. 19, 2000.

FIELD OF THE INVENTION

This invention relates to non-invasive cardiovascular assessment. More particularly, the invention relates to non-invasive assessment of aortic compliance and other cardiovascular parameters by analyzing signals recorded with a sensor having a transducer.

BACKGROUND OF THE INVENTION

The signals recorded with a sensor placed beneath a blood pressure cuff are termed "suprasystolic" signals if the cuff pressure is above the subject's systolic blood pressure. In addition, signals can be recorded when the cuff pressure is below systolic pressure. In all cases, the signals result from pressure energy transmissions and are dependent upon the subject's physiology. FIG. 1 shows typical signals for cuff pressures both above and below systolic, from a piezoelectric sensor.

When the heart pumps, a pressure gradient is generated within the cardiovascular system. This results in pulse pressure waves traveling peripherally from the heart through the arteries. Like any wave, they reflect back off a surface or other change in impedance. Arterial pulse waves reflect back from both the peripheral circulation and from the distal aorta when it becomes less compliant (Murgo, Westerhof et al. 1980; Latham, Westerhof et al. 1985). These reflection waves are identifiable in arterial pressure tracings, but the exact timing and magnitude of the waves are difficult to discern. Nevertheless, they have been the basis of several commercial systems to assess reflectance waves. These systems measure arterial contours using applanation tonometry from the radial artery.

If a low frequency sensor is placed over the brachial artery beneath a blood pressure cuff and the cuff is inflated above systole, suprasystolic signals can be recorded (Blank, West et al. 1988; Hirai, Sasayama et al. 1989; Denby, Mallows et al. 1994). An idealized suprasystolic signal for one heart beat is shown in FIG. 2. These signals contain frequency components of less than 20 Hertz, which are non-audible. Suprasystolic low frequency signals provide clear definition of three distinct waves: an incident wave corresponding to the pulse wave and two subsequent waves. Blank (Blank 1996) proposed that the second wave emanated from the periphery and the relative amplitude of this wave to the incident wave (K1R) was a measure of peripheral vascular resistance (PVR). He proposed a constant such that PVR could be measured from the ratio of the incident to the first reflectance wave. See, also, U.S. Pat. No. 5,913,826, which is incorporated herein by reference in its entirety.

The second suprasystolic wave is, in fact, a reflectance wave from the distal abdominal aorta—most likely originating from the bifurcation of the aorta and not from the peripheral circulation as proposed by Blank. This has been verified in human experiments (Murgo, Westerhof et al. 1980; Latham, Westerhof et al. 1985) and in our studies using pulse wave velocity (PWV) measurements. The relative amplitude of the first reflectance wave is therefore a measure of the stiffness, compliance, or elasticity of the abdominal aorta rather than peripheral resistance.

In the clinical experiments upon which Blank relied to formulate his hypothesis, changes in compliance were induced with epinephrine and epidural anesthesia. The changes in compliance were accompanied by changes in peripheral resistance. Thus, he saw a relationship between his K1R and PVR, but it was a co-variable and not a true association.

The third wave occurs at the beginning of diastole and is believed to be a reflection wave from the peripheral circulation. As such, it is a measure of peripheral vasoconstriction. Suprasystolic signals can be utilized to measure compliance by relating the amplitude of the first wave (incident or SS1) to the amplitude of the second (aortic reflection or SS2) wave. The degree of vasoconstriction can be assessed by measuring the amplitude of the diastolic or third wave (SS3 wave) and relating it to the SS1 wave. Amplitudes, areas under the curves, or other values calculated from the waves can be utilized. Data has been analyzed by measuring amplitudes, ratios of amplitudes and time delays between waves.

OBJECTS OF THE INVENTION

It is therefore an object of the invention to provide non-invasive cardiovascular assessment.

It is also an object of the invention to provide non-invasive assessment of aortic compliance by analysis of suprasystolic signals.

It is a further object of the invention to provide a system for assessing cardiovascular status non-invasively, said system comprising an external peripheral pressure cuff, a wideband external pulse transducer, and a computing device for computing desired values.

It is a yet further object of the invention to provide a method for determining a compliance value comprising the steps of measuring a pressure waveform of a peripheral artery with blood flow occluded, measuring the difference in amplitude between a first suprasystolic peak and first suprasystolic trough, measuring the difference in amplitude between a second suprasystolic peak and a second suprasystolic trough, and determining the ratio of the two differences.

It is still another object according to the present invention to provide a non-invasive cardiac monitoring system comprising a brachial artery cuff, a pressure control system for said cuff, a wideband acoustic transducer for measuring wideband acoustic emissions from the brachial artery, and a system for analyzing an output from the wideband acoustic transducer to produce data indicative of cardiac status.

These and other objects of the invention will become more apparent in the description below.

SUMMARY OF THE INVENTION

This invention is directed to a reliable system to acquire suprasystolic signals from patients, a method to analyze the signals, and clinical applications for the signals. The system consists of a low frequency transducer placed beneath a blood pressure cuff placed around a patient's arm. The signals are amplified, passed through an analog to digital converter and transferred to a computer or processor for analysis. Analyzed signals will be stored, presented on a screen numerically or graphically. Data can be stored or transmitted to databases or other health care facilities.

An important aspect of this invention is the measurement device. A variety of transducers can be used. The transducer must be able to record signals as low as about 0.1 Hertz and be sturdy enough to withstand external pressures of about 300 mmHg. For example, a more commercially available piezoelectric transducer consists of two adjacent sensors approximately 1.5 cm in diameter. The transducer is placed along the axis of the brachial artery providing proximal (closer to the heart) and distal signals. Preferably only one sensor is used. However, an alternative is to use an array of sensors to aid in noise elimination in certain clinical environments. Another possibility is to incorporate inexpensive sensors into a disposable blood pressure cuff to create a disposable product suitable for critical care environments where infection control is important.

A standard blood pressure cuff can be used, such as, for example, a radiofrequency welded blood pressure cuff (without a separate bladder) manufactured by CAS Medical Systems Branford, Conn., USA. The sensor is attached to the inside of the cuff, with use of a suitable attachment means, such as VELCRO strips. Preferably, the sensor is approximately 1 to 1.5 cm from the distal border of the blood pressure cuff. The blood pressure cuff is then applied around the arm with the sensor on the medial aspect of the arm, overlying the brachial artery (as shown in FIG. 7). Exact location does not appear to be critical. This is one of the attractive features of this system as it is simple to apply and unlikely to be technician-dependent like other technologies currently used to assess aortic compliance. The lead from the sensor and air hose from the blood pressure cuff are attached to a recording device. An extensive discussion of equipment useful according to the invention is set forth in U.S. Pat. No. 5,913,826, incorporated herein by reference.

A controllable pump will inflate the blood pressure cuff above systole and the cuff will then slowly deflate to measure systolic and diastolic pressures. The pump will then inflate the cuff to a set value above systole (e.g., 40 mmHg) and sustain this pressure for a period of time (e.g., 10 seconds), then deflate. An alternative is to inflate the cuff to determine systole, then reinflate 40 mmHg above systole, sustain the pressure for 10 seconds, then rapidly deflate to just below systole, deflate slowly to define diastole, then deflate to zero. Other methods may also be employed; however, the important aspect is that systole is determined prior to measuring suprasystolic beats.

The signals will be analyzed and can be presented as numerical values in a variety of ways, on a screen, as a printout, stored in a computer, or transferred via infrared or modem to remote sites for analysis or archival. Data can also be presented on a screen or other display device as waveforms for visual inspection. This can be stored as such and retrieved for comparison at a future date. Likewise, waveforms can be transmitted over phone lines, the Internet, etc. for inspections or analysis at a remote sites. One option is not to analyze signals at the site of the patient, but to send the signals to a central location where analysis will be performed and a detailed report returned relating interpretation of the signal to a large database of signals.

Analysis of the suprasystolic waveforms will include the amplitudes of the SS1, SS2, and SS3 signals and the time interval between the signals to provide an array of physiological data. Ratios between waves can be determined on the basis of amplitude, areas under the curves or by other variables such as rate of change of the slope.

Aortic compliance can be determined by the ratio of SS1 to SS2. The preferred simple method is described below wherein the amplitude of the descending slope of SS1 is compared to the descending slope of SS2 (SS1/SS2 ratio). Alternatively, the areas under the curves of SS1 to SS2 can be determined. The SS1/SS2 ratio is used as an index of compliance. Compliance, expressed in mL/mmHg, can be derived from a relationship of the forms given below, and equations (6) and (7).

Pulse wave delay can be used as an adjunctive measure of aortic compliance by calculating the delay between the peaks of SS1 and SS2 and illustrated in FIGS. 10(a) to 10(c). This does not measure PWV as the distances from the aorta to iliac arteries are not measured.

Systolic and diastolic pressures can be determined from the onset and offset of K2 signals as previously described. Alternatively, systole and diastole can be obtained by frequency analysis as shown in FIG. 8. Pulse pressure can be determined from the difference between systole and diastole. For example, with a measured systolic pressure of 130 mmHg, and diastolic pressure of 70 mmHg, the pulse pressure is given by 130−70=60 mmHg.

Compliance is measured by first determining the SS1/SS2 ratio. Compliance is derived from equations such as equation (6) or (7). Pulse pressure is measured from the blood pressure. Stroke volume is then calculated using equation (4).

For example, in FIG. 10(a) the SS1/SS2 ratio is 8.3. Using equation (6) a compliance of 1.86 can be calculated. Pulse pressure is 40 mmHg (as the blood pressure is 90/50). Therefore, using equation (4) a stroke volume of 74 mL is calculated.

Heart Rate (HR) can be measured from the time delay between beats. Cardiac output (CO) is stroke volume (SV) multiplied by heart rate, that is:

$$CO = SV \times HR \qquad (1) \text{ Cardiac Output}$$

The size of the SS3 is a measure of the degree of peripheral vasoconstriction. This can be assessed as (1) the amplitude of SS3, (2) the ratio of SS1 to SS3, or (3) the area under the SS3 curve. An example of an increase in SS3 is seen in FIG. 15 with the cold pressor test. SS3 increased from 0.12 to 0.25 V by placing the patient's hand in ice water. The SS1/SS3 ratio decreased from 3.5 to 1.3.

The amplitude of SS1 and the rate of change of pressure of SS1 (dV/dt) can be determined. In FIG. 13 the amplitude of SS1 at rest was 0.27 V and the rate of change is 4.5 V/sec. Following exercise, the amplitude of SS1 increased to 0.55 and the dV/dt more than doubled to 11.0 V/sec.

Variations in the suprasystolic signals (amplitude of SS1 and SS3, time intervals between SS1 and SS2 and ratios of SS1/SS2 and SS1/SS3) will be generated from a series of beats collected from the suprasystolic signal. This could be reported as a percentile change, which can be related to perturbation of the circulation by respiration. This can be used as a measure of respiratory distress or as a measure of volume depletion. This feature can be incorporated into the physiological monitor but will also be useful as a screening monitor in emergency rooms and physicians' offices.

Heart rate can be derived by beat-to-beat delay. Beat-to-beat variability in heart rate can be measured. Arrhythmias can be detected by the variability of inter-beat duration and in the variability in morphology of suprasystolic signals as shown in FIG. 20, for example. The duration of systole and diastole can be determined from suprasystolic signals, as is described below.

Age-adjusted changes in SS1/SS2, SS1/SS3 ratios, time delays between SS1 and SS2, amplitudes of SS1, etc., will be constructed to provide a vascular age profile for particular populations.

Specific morphological features of the suprasystolic signals may aid in diagnosis of specific vascular conditions, e.g.:

Bifid suprasystolic signals are an index of low stroke volume or shock.

Bifid or prolonged SS3 relates to increased peripheral vasoconstriction.

Suprasystolic beats can be analyzed in a variety of ways to provide a variety of parameters useful for cardiovascular diagnosis, management and treatment of disease, prognostic information and as a physiological monitor. Specific applications will be presented below.

Alterations in aortic compliance can be used to detect early onset and define the degree of arterial disease. This technology will provide prognostic information and as such, will be used as a screening device. Age-adjusted predictors of the risk of vascular disease can be generated, overall or for specific patient populations.

The response of the suprasystolic signals to physiological stresses may also be used to aid in diagnosis. It is known that alterations in endothelial dysfunction (ED) antedate the clinical development of overt clinical vascular disease. ED may be detected by providing a physiological stimulus and detecting the degree of change in arteries to the stimulus. For example, moderate exercise may result in a greater increase in compliance in healthy vessels. By contrast, the cold pressor test may result in an augmented response in patients with early hypertension or early preeclampsia. Changes in suprasystolic measurements of compliance or peripheral vasoconstriction or stroke volume to cold pressor test, mild exercise, or the administration of drugs such as nitroglycerin or acetylcholine can be used as a marker of endothelial dysfunction and thereby as a prognostic tool.

Compliance changes with medical therapy, including administration of antihypertensive agents, cholesterol-lowering agents, female sex hormone, exercise training and certain dietary approaches. Assessing the need for treatment and monitoring the effectiveness of treatment can be guided by suprasystolic waveform analysis.

Heart failure is a complex disorder arising from a variety of causes. It is characterized by an increase in peripheral vasoconstriction and usually a reduction in cardiac contractility or stroke volume. FIG. 3 shows a waveform of a patient with severe heart failure and demonstrates these phenomena. These factors can be followed over time using suprasystolic waveform analysis to aid treatment.

Hypertension is characterized by reduced arterial compliance, endothelial dysfunction and peripheral vasoconstriction. Increased stroke volume is often noted in early hypertension. Reflected aortic waves (SS2) augment mid to late systolic pressure increasing the strain on the heart. Suprasystolic waveform analysis can guide treatment. Firstly, it might suggest one form of therapy over another. Secondly, the effectiveness of treatment can be assessed by not only a reduction in blood pressure but also by an increase in aortic compliance, a decrease in vasoconstriction or a normalization of cardiac output.

Preeclampsia results in alterations in aortic compliance and peripheral vasoconstriction. Analysis of suprasystolic signals can be used to diagnose preeclampsia, provide an early diagnostic prediction that preeclampsia will develop and aid in distinguishing between hypertension per se and preeclampsia.

Suprasystolic signal analysis may be used by the insurance industry as a guide to prognosis and as such, utilized for actuarial purpose.

This technology can detect physiological changes associated with anesthesia not hitherto possible with non-invasive monitoring. Changes in compliance, peripheral vasoconstriction, stroke volume, cardiac contractility and circulation with ventilation can be used as a monitoring system during anesthesia. The data can be stored and displayed on a screen to provide changes in parameters over time. This can help adjust anesthetic depth and guide response to drug and fluid therapy.

A similar system will be useful in intensive care, high acuity monitored settings, emergency rooms, obstetric delivery units, ambulances and remote sites.

Shock is a clinical state with inadequate blood flow for tissue needs. Causes include hypovolemic or hemorrhagic shock and septic shock from bacterial sepsis. Shock or circulatory collapse can also occur during anesthesia.

Circulatory collapse and hemorrhagic shock are associated with low stroke volume, low cardiac output, low blood pressure and a predilection for oscillation of blood pressure and stroke volume with ventilation. Suprasystolic waveform analysis can aid in the diagnosis of shock.

Two cases are described: one hemorrhagic and one during spinal anesthesia. FIG. 4 demonstrates minimal variation of waveforms with ventilation during anesthesia. Blood pressure of 125/70, heart rate 87 and stroke volume 137 mL are normal values. Following major blood loss, blood pressure falls to 70/50. Suprasystolic signals change and manifest significant fluctuation with ventilation as seen in FIG. 5. Stroke volume is calculated to vary from 23 to 32 depending upon the phase of ventilation. Following administration of blood, signals are restored.

In contrast, FIG. 14 represents a patient who had a reduction in blood pressure and heart rate with extensive spinal anesthesia. This was accompanied by changes in SS1/SS2 ratios demonstrating that stroke volume and cardiac output had declined significantly.

Suprasystolic signals can be utilized for a variety of purposes, including vascular assessment and monitoring response to treatments, etc. The technology can also be used as a routine screening of heart rate or for the presence of respiratory difficulty or arrhythmias. In addition, the waveforms can be automatically compared to the prior recordings from the same patient. This could provide the basis for an information system for physicians' offices.

Because the signals are in digital form, they can be transmitted by phone, internet, satellite, etc. providing the ability for a central data analysis and storage. In addition, it provides the opportunity for remote site data collection: outer space, mountaineering or in regions without direct physician access. Home monitoring is also possible as a stand-alone monitor or via links to central data analysis or to physicians' offices or hospital.

BRIEF DESCRIPTION OF THE DRAWINGS

FIG. 1 represents a typical signal from a piezoelectric sensor;

FIG. 2 represents an idealized suprasystolic signal;

FIG. 3 represents a suprasystolic waveform for a heart failure patient;

FIG. 4 represents suprasystolic beats during anesthesia with a patient on a ventilator;

FIG. 5 represents suprasystolic beats of a patient in shock, where beats 7 and 8 are with a ventilator;

FIG. 6 represents the frequency response of a sensor;

FIG. 7 is a schematic representation of placement of a sensor;

FIG. 8 represents the energy content of recordal beats;

FIGS. 9(a) and 9(b) are block diagrams of the measurement device interface with a subject and a computer, respectively;

FIGS. 10(a), 10(b), and 10(c) are representative suprasystolic waveforms for (a) a young person, (b) moderately reduced compliance, and (c) an elderly person with hypertension, respectively (vertical axis is volts);

FIG. 11 represents a correlation between a suprasystolic signal and ascending aorta pressure;

FIGS. 12(a) and 12(b) represents suprasystolic waveforms for a matched pregnant woman without preeclampsia and with preeclampsia, respectively;

FIGS. 13(a) and 13(b) represent suprasystolic waveforms of subjects before and after mild exercise, respectively;

FIGS. 14(a), 14(b), and 14(c) represent suprasystolic waveforms during spinal anesthesia: initially, after extensive anesthesia, and after administration of ephedrine, respectively;

FIGS. 15(a) and 15(b) represent suprasystolic waveform morphology after (b) the cold pressor test compared to (a) prior measurements;

FIG. 16 represents the determination of PWV from invasive pressure tracings;

FIG. 17 is a schematic representation of suprasystolic wave paths;

FIGS. 18(a) to 18(d) represent the regression of suprasystolic parameters against age;

FIG. 19 represents the relationship between SS1/SS2 and compliance;

FIG. 20 represents an example of arrhythmia in a suprasystolic waveform, where (A) is normal and beat (B) is ectopic;

FIG. 21 represents the affect of normal respiration on suprasystolic waveforms;

FIG. 22 represents changes in suprasystolic signal due to labored breathing; and FIG. 23 represents a suprasystolic waveform during Valsalva Maneuver, where the shaded region indicates beats affected by the maneuver.

DETAILED DESCRIPTION OF THE INVENTION

Arterial compliance refers to the stiffness of arteries. In young healthy people, arteries are compliant so that a volume of blood ejected causes them to distend more for a given pressure. By contrast, stiff arteries (arteries with a low compliance) distend less. Compliance (C) is measured by the change in volume (dV) per unit increase in pressure (dp) (Brinton, Cotter et al. 1997; de Simone, Roman et al. 1999):

$C=dV/dp$     (2) True compliance

Compliance can be measured fairly accurately by stroke volume (SV) divided by pulse pressure (PP) even though the arterial circuit is not a totally closed system (Chemla, Hebert et al. 1998):

$C \approx SV/PP$     (3) Estimated compliance

Arterial compliance, although important, is not commonly measured in clinical practice, as the measurement is difficult to perform. Pulse pressure is easy to measure using a blood pressure cuff, but stroke volume is more difficult. Studies have measured stroke volume with echocardiography, pulmonary artery catheters, radio nuclide scans or magnetic resonance imaging (MRI)—all expensive or invasive techniques. For this reason, accurate measurement of compliance remains a research technique at this point in time.

Arterial compliance can also be derived from the rate of change of pressure from the aortic pressure contour, if peripheral vascular resistance is known (Liu, Brin et al. 1986). Peripheral vascular resistance can only be calculated if cardiac output (CO) can be measured. This limits the utility of the technique.

Compliance can also be derived from the diastolic pressure decay of the pulse contour of a peripheral pulse using certain assumptions. This technique, however, has limited value when pulse rates are high as the diastolic phase is incomplete.

Compliance can be measured by imaging an artery with ultrasound or MRI and determining the change in arterial volume between systole and diastole. This requires expensive equipment and is technician-dependent, and reproducibility may be a problem. Nevertheless, imaging of the thoracic aorta or carotid artery is used to a limited extent in clinical studies.

Clinically, the most commonly used means of assessing compliance is to measure pulse wave velocity (Lehmann, Riley et al. 1997; Blacher, Asmar et al. 1999). Pulse wave velocity (PWV) is related to compliance of blood vessels such that PWV is higher in non-compliant vessels. This technique does not measure compliance per se, but provides an indication of arterial compliance. In practice, it requires a sensor to be placed over both the carotid (neck) and femoral (groin) arteries and the delay between the pulses recorded at the sensors to be measured. The technique is somewhat cumbersome and uses either ultrasound or piezoelectric sensors.

Another clinically used means of assessing compliance (but not actually measuring it) is determining pulse augmentation index (Yasmin and Brown 1999). Pressure pulse waves travel into the arterial circuit and are reflected back from the distal aorta causing an augmentation of the aortic pulse pressure (as shown in FIG. 8). If the aorta is stiff, the pulse wave travels rapidly and is reflected more completely from the distal aorta. This leads to marked augmentation of the aortic pressure. By contrast, if the distal aorta is compliant, less reflection occurs resulting in less augmentation.

Arteries normally have a muscular layer, as well as elastic fibers. With hypertension, aging, and arteriosclerosis, elastic fibers breakdown and the arteries become stiffer with increase in fibrous tissue, cholesterol deposits and hypertrophy of the encircling muscle. These changes affect compliance.

Arterial compliance is therefore clinically important for several reasons. First, it is a measure of arterial disease. Aging, atherosclerosis and hypertension all decrease aortic, coronary, and carotid artery compliance. It is known that patients with less compliant vessels have reduced life expectancy. And second, an improvement (increase) in compliance reduces blood pressure and improves cardiac performance. This leads to less strain on the heart and improved exercise tolerance. This is particularly important in the management of hypertension and heart failure. Treatment modalities which improve compliance include antihypertensive drugs, female sex hormones, cholesterol lowering drugs, physical exercise and exercise training. The ability to monitor arterial compliance would enhance patient care in these areas.

Compliance measurements have been performed in clinical studies by utilizing aortic pulse wave velocity, applanation tonometry of the radial or carotid arteries, or ultrasonic assessment of the carotid arteries. These studies have demonstrated that patients with atherosclerosis and hypertension have less compliant arteries (Blacher, Asmar et al. 1999; Bortolotto, Blacher et al. 2000; van Popele, Grobbee et al. 2001). Suprasystolic measurements of compliance will provide similar results but more simply and at less cost. For this reason, this technology can be used to detect the presence and severity of vascular diseases.

Disease and aging of arteries affect the aorta, carotid, and coronary arteries to a similar extent. Arteries of the upper extremities are affected less. Thus, aortic compliance is strongly related to overall compliance and is, in addition, a good measure of vascular risk.

The method of the invention is similar to conventional blood pressure measurement except that the stethoscope is replaced with a sensor having a transducer, preferably a transducer with a frequency range of from about 0.1 to at least 1000 Hz. A typical frequency response of a sensor useful according to the invention is shown in FIG. 6.

According to the invention, a sensor 2 having a proximal edge 4 and a distal edge 6 is placed over the brachial artery 8 under the blood pressure cuff 10 about one centimeter from distal edge 6, as shown in FIG. 7. Recordings from sensor 2 are preferably amplified, passed through an analog to digital converter, and displayed on a PC using, for example, National Instruments LabView Software. Further analysis of the waveform can be performed using software such as the Matlab software from The Mathworks Inc.

Following application of the blood pressure cuff and sensor, the cuff is inflated above systolic pressure and then deflated slowly to allow for recording of each pulse signal. FIG. 1 represents a typical recording. Suprasystolic (K1), subdiastolic (K3) and beats between systole and diastole (K2) can be detected. Systole and diastole can be characterized by the onset and offset of higher frequency (audible) signals as shown in FIG. 8. The suprasystolic signals are then recorded and analyzed.

The equipment used in the studies incorporated a CardioDyne NBP2000 (Luxtec Corporation) blood pressure monitoring system, which had been modified to provide the requisite bandwidth (as shown in FIG. 6). The unit had an automatic inflation-deflation system with the rate of deflation adjusted to 3 mmHg per heart beat. An EKG input facilitated the deflation mechanism. Signals were then recorded on a PC. Some specific details about the equipment configuration are given in FIGS. 9(a) and 9(b).

Three representative signals are shown in FIGS. 10(a) to 10(c). In FIG. 10(c), the subject was an 85 year old with hypertension of 160/85. The compliance values indicated in FIGS. 10(a) to 10(c) range from 1.86 to 0.67, which is significant in that the varying compliance values reflect the varying condition of the patients' cardiovascular systems.

It is instructive to compare FIG. 1 with FIGS. 10(a) to 10(c). In the latter cases, seven points have been identified:
 1. Trough before the incident SS1 wave
 2. Peak of SS1 wave
 3. Trough following SS1 wave
 4. Peak of aortic reflectance wave—SS2
 5. Trough following SS2
 6. Peak of SS3 wave
 7. Trough of next incident wave Analysis of the waves includes the identification of the following, using the notation Vn for the voltage at point n, and tn for the absolute time at that point:
 1. Height of SS1 wave=V2−V1
 2. Time delay from 1−2=t2−t1
 3. Duration of systole=t5−t1
 4. Duration of diastole=t7−t5
 5. Measure of Compliance: SS1/SS2 ratio (V2−V3)/(V4−V5)
 6. Measure of pulse wave velocity: Aortic transit time=t4−t2
 7. Measure of vasoconstriction: SS1/SS3 ratio=(V2−V3)/(V6−V5)
 8. Measure of vasoconstriction: Amplitude of SS3 above baseline=V6−V1

Measures 5, 6, 7 and 8 have been chosen on the basis of clinical understanding and, although somewhat arbitrary, were used in the following studies as a means of measuring aortic compliance and peripheral vasoconstriction.

During cardiac catheterization in 20 patients, ascending aortic pressure tracings were recorded concomitantly with the suprasystolic recordings using the EKG as a time reference. An example of such a tracing is shown in FIG. 11. The three curves from the ascending aorta represent three separate beats plotted against the suprasystolic signal. It can be seen that the incident wave SS1 corresponds with the upstroke and initial phase of the aortic pressure tracing and that the rate of change of pressure from the aortogram is similar to the upstroke of the SS1. This verifies that the characteristics of SS1 can be used as measure of contractility of the heart.

The SS2 occurs in mid to late systole and corresponds to the augmentation wave discussed below. Also, the trough following the SS2 corresponds with the dicrotic notch signifying the end of systole, and the SS3 is a diastolic wave.

To determine whether the pattern of the suprasystolic beats varied above systole, beats were recorded at 3 mmHg intervals in 37 subjects by inflating the blood pressure cuff to between 45 and 100 mmHg above systole. Time intervals and the amplitude of points were plotted for each pressure. The time intervals are found to be relatively stable over a range of suprasystolic pressures. By contrast, the amplitude or voltage of the signals varied, especially as the cuff pressure approached systole. For this reason, it is important to determine systole initially and then inflate the cuff to a standard value above systole for the purpose of recording suprasystolic beats. Resulting analysis suggested a value between 40 and 50 mmHg above systole is optimal to provide reliability yet minimize discomfort to patients.

As mentioned previously, arterial compliance is not currently utilized as a physiological monitoring variable in clinical practice due to difficulty in assessing it. Nevertheless, arterial compliance changes markedly under different physiological states suggesting it could be a useful physiological variable to monitor. Furthermore, if compliance could be measured, then stroke volume could be calculated using equation (3).

Stroke volume (SV) is the volume of blood pumped by the heart with each beat expressed in milliliters. Normal SV at rest is 70–80 mL for the average adult. This is an important physiological parameter, dependent upon the strength of the heartbeat and the resistance to flow in the arterial circuit. SV increases with physical exercise and will fall with heart failure or from shock.

SV is not easy to measure, requiring invasive equipment (e.g., pulmonary artery catheters) or expensive imaging devices such as ultrasound or MRI. A number of non-invasive means of assessing SV from peripheral arterial waveforms have been proposed, but none are accurate. A simple way to measure SV non-invasively would be advantageous in a number of clinical settings, for example intensive care, during surgery, emergency rooms, obstetrics and in the management of patients with heart disease.

The aorta distends in systole (if compliant), accommodating the stroke volume. Thus, measuring aortic compliance (C) provides an opportunity to derive stroke volume (SV) from its relationship with pulse pressure (PP) as given in equation (2). Thus:

$$SV = C \times PP \quad (4) \text{ Stroke Volume from Compliance}$$

Pulse pressure can be accurately determined from measured systole and diastole with this monitoring technique (Blank, West et al. 1988; Hirai, Sasayama et al. 1989). By deriving a relationship between the SS1/SS2 ratio and compliance measured in a series of patients using equation (3), one can then calculate an estimate of SV from measured SS1/SS2 ratios. To establish the relationship of SS1/SS2 to compliance, measurements of stroke volume and pulse pressure must be obtained in a large sample of patients. A relationship has been formulated based upon preliminary data and is shown in FIG. 19. The actual form of the fitting function should be determined from a larger sample. However, it appears at this stage than both logarithmic and power function regressions are good candidates. Thus, we have the following preliminary relationships:

$$C = 1.011 + 0.402 \ln(SS1/SS2) \quad (6) \text{ Logarithmic fit for compliance}$$

$$C = 1.018 \, (SS1/SS2)^{0.257} \quad (7) \text{ Power function fit for compliance}$$

where ln denotes the natural logarithm. However, it is within the scope of the invention that useful compliance values can be generated from broader ranges. For example, compliance could be calculated from an equation of (from about 0.90 to about 1.20) plus (from about 0.35 to about 0.45) times the natural log of (SS1/SS2) or (from about 0.90 to about 1.20) times (SS1/SS2) times (from 0.225 to about 0.275).

Compliance is known to be increased by physical exercise (Joyner 2000), anesthetic agents, and the administration of nitroglycerin. The physiological mechanism is via reduction of sympathetic nervous system activity and by release of nitric oxide from the endothelium, which dilates the smooth muscle encircling the arteries. By contrast, acute reductions in arterial compliance are caused by discharge of the sympathetic nervous system and vasoconstrictive agents (such as norepinephrine). Many of these physiological responses not only alter arterial compliance but also have concomitant effects on peripheral vasoconstriction.

The responsiveness of the monitoring system to known physiological states, which acutely influence arterial compliance, has been tested. Four separate interventions were studied—exercise, spinal anesthesia, sublingual nitroglycerin and immersing the hand of a subject in ice water (the so called "cold pressor" test).

Mild physical exercise was performed in 20 subjects of different ages (19–65) to achieve a heart rate of 100–120 beats per minute. Suprasystolic signals were measured before, immediately after, and 3 minutes following exercise. SS1/SS2 ratios increased in 18 of the 20 subjects, usually by a factor of between 2 and 3 when comparing pre- and immediately post-exercise waveforms. SS1/SS3 ratios often increased as well, suggesting peripheral vasodilatation. The amplitude of the SS1 tended to increase. These changes suggest an increase in compliance, reduction in peripheral vasoconstriction, and an improvement in stroke volume. Typical tracings for before and after exercise are shown in FIG. 13. Note the increase in compliance, stroke volume, heart rate, blood pressure, cardiac output and dV1/dt1 as a result of the exercise.

In one very fit male, two intensities of exercise were performed and values of stroke volume calculated based upon our algorithm. Stroke volume at rest was 81 mL. It increased to 133 mL with moderate exercise. Following very vigorous exercise, stroke volume was 212 mL; SV returned to 95 mL following a period of rest.

The response to sublingual nitroglycerin was determined in 4 patients undergoing coronary angiography. A 2-fold increase in SS1/SS2 was noted (indicating an increase in arterial compliance) but change in the degree of peripheral vasoconstriction (as evidenced by changes in SS1/SS3) was less evident.

Changes in suprasystolic signals following spinal anesthesia in 20 elderly men undergoing prostatectomy were determined. In 15 patients, the level of spinal anesthesia was localized and the changes in circulatory physiology minimal. In these patients, SS1/SS2 ratios and SS3 voltages were unchanged or increased slightly, verifying a preservation of arterial compliance and peripheral vasoconstriction. However, in 5 patients, the anesthesia was more extensive resulting in more profound changes in blood pressure requiring administration of ephedrine, a vasopressor, to restore circulatory function. Changes in suprasystolic beats were seen in all of these patients. A typical signal is shown in FIG. 14 for a patient who developed hypotension and a slow heart rate in response to the spinal anesthesia. By using our algorithm (described below) to measure stroke volume, we calculated that stroke volume fell from 97 to 63 mL and cardiac output declined from 6.9 L to 3.3 L. Following administration of ephedrine, SV increased to 80 mL and CO to 6 L. Note in the figure the drop in dV3 with extensive spinal and its augmentation with ephedrine.

The cold pressor test was applied in 6 subjects by immersing the contralateral hand in ice water for three minutes and recording the suprasystolic signals. The SS1/SS2 ratio decreased in all subjects by a factor of 2 to 3, indicating a decrease in compliance. Measures such as the SS1/SS3 ratio indicated increases in peripheral vasoconstriction. A typical pair of tracings is shown in FIG. 15. Note too that stroke volume and cardiac output change very little.

The pulse wave travels from the heart to the distal aorta and back to the heart, and then passes down the arm where it is detected as the SS2 signal. The SS1 travels from the heart down the arm. Thus, the time delay between SS1 and SS2 is the time taken for the pulse to travel from the heart to the distal aorta and back to the heart (see FIG. 16). Recordings in over 100 adults of different ages have demonstrated SS1–SS2 time delays of 0.08 to 0.22 seconds. Assuming that the distance from the heart to the distal aorta is 50 cm, these correspond to pulse wave velocities of around 5 to 12 m/sec, about the normal ranges noted. Furthermore, in 20 patients undergoing coronary angiography, aortic pulse wave velocities were measured directly from ascending and distal aortic pressure tracings. An example of this analysis is illustrated in FIG. 17.

The measured pulse wave velocities were very similar to the values predicted from the SS1–SS2 values. Thus, the SS1–SS2 time delay is an indicator of pulse wave velocity, although not a measure as such as the length of the aorta is assumed to be unknown. This data is also confirmatory that the SS2 emanates from the distal aorta and not the periphery as Blank assumed.

Peripheral vasoconstriction refers to the state of contraction of small arteries and arterioles in the peripheral circulation. Similar to large arteries, peripheral vasoconstriction is under the control of the autonomic nervous system and is also modulated by an array of factors including circulatory hormones (adrenaline, angiotensin) and local factors such as nitric oxide.

Increased vasoconstriction reduces blood flow to organs, may increase blood pressure and put a strain on the heart. By contrast, vasodilatation may lead to a drop in blood pressure.

Peripheral vasoconstriction is typically assessed by deriving peripheral vascular resistance (PVR) given a known mean arterial pressure (MAP) and cardiac output (CO):

$$PVR = MAP/CO \quad (5) \text{ Peripheral Vascular Resistance}$$

PVR may also be assessed from pulse signals measured in the radial artery using assumptions similar to those utilized in determining compliance.

Increased vasoconstriction is seen with heart failure, preeclampsia and hypovolemic shock. Vasodilatation is seen in bacterial sepsis, hyperpyrexia and anesthesia. A simple measure of vasoconstriction would be clinically useful in clinical practice especially intensive care, obstetrics, surgery and emergency room settings.

Age results in reduced compliance of the aorta. Age also is associated with increased atherosclerosis and hypertension, which further reduces compliance (Bulpitt, Rajkumar et al. 1999). FIG. 18 shows suprasystolic values plotted against age for 33 normal subjects studied so far. Part (a) shows regression of the time between SS1 and SS2, which is an average of pulse wave velocity. Part (b) shows the SS1/SS2 ratio. Part (c) shows the SS1/SS3 ratio. Part (d) is a regression of the amplitude of SS3 versus age.

It is envisioned that a large database will be generated, which may be used to calculate an age-adjusted aortic compliance or vascular age range for patients. Such databases can be generated for subpopulations (e.g., obstetrics), ethnic groups and different population to provide more specific age-adjusted vascular risk profiles.

Arteries have a muscular layer, which can dilate or constrict. The tone of the muscular layer of the large arteries is controlled by the sympathetic nerves as well as by signals derived from the endothelium or inner layer of the artery. Dysfunction of the endothelium is believed to be a precursor to arterial disease resulting in less compliant arteries. Currently, endothelial dysfunction (ED) is measured by changes in the diameter of the brachial artery with certain stimuli. A reduced dilatation from a vasodilatory stimulus such as ischemia or exercise is a measure of impaired endothelial dysfunction. Patients with poor endothelial dysfunction have increased risk of coronary artery disease and vascular death (Sharma and Andrews 2000).

The problem with assessing ED currently is that it is done by measuring changes in the diameter of the brachial artery with expensive ultrasound equipment. Furthermore, the brachial artery is a vessel not commonly affected by vascular diseases. A simple way of assessing changes in arterial responsiveness as a marker of endothelial dysfunction in a clinically relevant artery such as the aorta would be useful.

Preeclampsia is a disease of pregnancy of unknown etiology which leads to pathology of the arterial system resulting in a reduction in blood flow to the placenta, kidneys and in the advanced stages, liver, brain and heart. It is a major cause of maternal and fetal mortality and morbidity, affecting 5–7% of pregnancies. Currently, diagnosis is made on the basis of onset of hypertension and protein in the urine. The only effective treatment is delivery of the baby. The condition is known to be associated with increased vasoconstriction and endothelial dysfunction (Roberts and Cooper 2001). To date, 6 preeclamptic and 4 normal pregnant control patients (matched by age, ethnic origin and gestation) have been studied. Analysis of suprasystolic signals demonstrated increased vasoconstriction (SS1/SS3 ratio) and reduced compliance (SS1/SS2 ratio) in all preeclamptic patients. FIG. 12 shows a comparison of typical waveforms for a preeclamptic woman and her control.

Analysis of the duration of systole and diastole can have diagnostic significance.

For example, it is advantageous to have a longer diastole in certain cardiac conditions to facilitate coronary perfusion and ventricular filling. Suprasystolic signals enable the timing of systole and diastole. These times have been measured. Systole tends to be relatively stable but was shortened following the Valsalva Maneuver, labored breathing and immediately after physical exercise.

Irregular heart rates can be detected by variations in beat-to-beat heart rate with this monitor. Heart rate can be determined by time delay between beats. The presence of an ectopic beat can be determined by profound differences between beats as seen in FIG. 20. Differences in amplitude and duration of SS1 and SS1/SS2 and SS1/SS3 ratios can be used to detect arrhythmias. Random heartbeats in atrial fibrillation can be also identified.

Arrhythmias are abnormal heartbeats and are usually considered to be an indicator of cardiac pathology. They are commonly diagnosed using an electrocardiogram (EKG). However, detecting cardiac arrhythmias is an important adjunct to a clinical screening monitor, which could identify the need to obtain an EKG. In addition, identification of ectopic beats is important as they should generally be excluded from analysis as they are not a normal beat.

Respiratory patterns have significant effects on circulatory function. Inspiration and expiration cause fluxes in venous return and transthoracic pressure leading to phasic changes in stroke volume and arterial pressure. These changes are most pronounced in patients with low blood volumes (or shock), patients with disordered autonomic nervous system function and when large fluxes in respiratory pressure are imposed (such as coughing, respiratory distress and patients on ventilators). There has been, to date, no easy way to assess these changes without invasive hemodynamic monitoring. These changes are of diagnostic importance especially in critical care environments such as intensive care, during surgery and in emergency rooms. Analysis of suprasystolic waves provides a non-invasive means of assessing changes in circulatory function with ventilation.

To demonstrate changes in suprasystolic signals with ventilation, the cuff pressure was inflated to 40 mmHg above systolic pressure. Subjects then (1) breathed quietly, (2) breathed through a straw to simulate labored breathing, and then (3) performed a Valsalva maneuver.

The changes over the respiratory cycle that occur with quiet breathing are minimal but present. Maximal changes in SS1/SS2 ratios, amplitude of SS1 and SS3 and time delay between SS1 and SS2 are shown in FIG. 21. Note the minimal changes. Breathing through a straw resulted in significant alterations in suprasystolic signals: a 6-fold variation in SS1/SS2 ratios; a 30% reduction in the amplitude of SS1 and a 50% range in the amplitude of SS3. These variations can be readily seen in FIG. 22.

Finally, the response to a Valsalva Maneuver was performed in several subjects. Valsalva Maneuvers are known to result in an acute reduction in blood pressure, stroke volume and abolition or reduction in aortic pulse wave reflection. Marked changes in amplitudes, ratios and time intervals are noted. The marked reduction in amplitude of the SS2 wave, increase in SS1/SS2 ratio and reduction in amplitude of the SS1 are consistent with the known physiological effects of the Valsalva Maneuver (Murgo, Westerhof et al. 1981) and are readily apparent in FIG. 23.

The studies described in this section verify that suprasystolic signals can be used to assess changes in circulatory physiology with ventilation.

Because of the variation in suprasystolic waves caused by ventilation, it is necessary to sample 5 to 10 beats at a specific suprasystolic pressure. This will provide information about both the average and the variability of suprasystolic parameters. The cyclic nature may enable respiratory rate to be calculated and for the range in values to be utilized as an index reflecting the effect of ventilation on the circulation.

The preceding specific embodiments are illustrative of the practice of the invention. It is to be understood, however, that other expedients known to those skilled in the art or disclosed herein, may be employed without departing from the spirit of the invention or the scope of the appended claims.

References

Blacher, J., R. Asmar, et al. (1999). "Aortic pulse wave velocity as a marker of cardiovascular risk in hypertensive patients." Hypertension 33(5): 1111–7.

Blank, S. (1996). "U.S. Pat. No. 5,913,826: Wideband external pulse cardiac monitor.".

Blank, S. G., J. E. West, et al. (1988). "Wideband external pulse recording during cuff deflation: a new technique for evaluation of the arterial pressure pulse and measurement of blood pressure." Circulation 77(6): 1297–1305.

Bortolotto, L. A., J. Blacher, et al. (2000). "Assessment of vascular aging and atherosclerosis in hypertensive subjects: second derivative of photoplethysmogram versus pulse wave velocity." American Journal of Hypertension 13(2): 165–71.

Brinton, T. J., B. Cotter, et al. (1997). "Development and validation of a noninvasive method to determine arterial pressure and vascular compliance." American Journal of Cardiology 80: 323–330.

Bulpitt, C. J., C. Rajkumar, et al. (1999). "Vascular compliance as a measure of biological age." Journal of the American Geriatrics Society 47(6): 657–63.

Chemla, D., J. L. Hebert, et al. (1998). "Total arterial compliance estimated by stroke volume-to-aortic pulse pressure ratio in humans." American Journal of Physiology 274(2Pt 2): H500-5.

de Simone, G., M. J. Roman, et al. (1999). "Stroke volume/pulse pressure ratio and cardiovascular risk in arterial hypertension." Hypertension 33(3): 800–5.

Denby, L., C. L. Mallows, et al. (1994). "Analysis of the wideband external pulse: An application of graphical methods." Statistics in Medicine 13: 275–291.

Hirai, T., S. Sasayama, et al. (1989). "Stiffness of systemic arteries in patients with myocardial infarction. A noninvasive method to predict severity of coronary atherosclerosis [published erratum appears in Circulation 1989 December; 80(6): 1946]."Circulation 80(1): 78–86.

Joyner, M. J. (2000). "Effect of exercise on arterial compliance." Circulation 102(11): 1214–5.

Latham, R. D., N. Westerhof, et al. (1985). "Regional wave travel and reflections along the human aorta: a study with six simultaneous micromanometric pressures." Circulation 72(6): 1257–69.

Lehmann, E. D., W. A. Riley, et al. (1997). "Non-invasive assessment of cardiovascular disease in diabetes mellitus." Lancet 350 Suppl 1: SI14-9.

Liu, Z., K. P. Brin, et al. (1986). "Estimation of total arterial compliance: an improved method and evaluation of current methods." American Journal of Physiology 251(3 Pt 2): H588–600.

Murgo, J. P., N. Westerhof, et al. (1980). "Aortic input impedance in normal man: relationship to pressure wave forms." Circulation 62(1): 105–16.

Murgo, J. P., N. Westerhof, et al. (1981). "Manipulation of ascending aortic pressure and flow wave reflections with the Valsalva maneuver: relationship to input impedance." Circulation 63(1): 122–32.

Roberts, J. M. and D. W. Cooper (2001). "Pathogenesis and genetics of pre-eclampsia." Lancet 357(9249): 53–6.

Sharma, N. and T. C. Andrews (2000). "Endothelial function as a therapeutic target in coronary artery disease." Curr Atheroscler Rep 2(4): 303–7.

van Popele, N. M., D. E. Grobbee, et al. (2001). "Association between arterial stiffness and atherosclerosis: the Rotterdam Study." Stroke 32(2): 454–60.

Yasmin and M. J. Brown (1999). "Similarities and differences between augmentation index and pulse wave velocity in the assessment of arterial stiffness." Qjm 92(10): 595–600.

Blank, U.S. Pat. No. 5,913,826

What is claimed is:

1. An apparatus for assessing cardiovascular status of a mammal comprising:
    a system for locally applying a pressure to an artery, capable of restricting blood flow through said artery;
    a wideband external pulse transducer having an output and situated to measure suprasystolic signals proximate to said artery; and
    a computing device receiving said output for assessing large arterial vascular compliance values from said suprasystolic signals.

2. The apparatus of claim 1, wherein said computing device analyzes a temporal amplitude pattern of said output.

3. The apparatus of claim 2, wherein said system for locally applying a pressure to an artery occludes said artery, said temporal amplitude pattern comprises a series of adjacent amplitude peaks and related dips, and the computing device calculates a first ratio of (1) the amplitude difference of a first peak and a subsequent dip and (2) the amplitude difference of a second peak and the subsequent dip as well as a second ratio of (1) the amplitude difference of the first peak and a subsequent dip and (2) the amplitude difference of a third peak and a subsequent dip.

4. The apparatus of claim 3, wherein the computing device calculates said value as a function of the natural logarithm of said first ratio or a power function of said first ratio.

5. The apparatus of claim 1 which assesses whether a pregnant mammal has a preeclampsia condition.

6. The apparatus of claim 1 which assesses whether a pregnant mammal has cardiac insufficiency.

7. The apparatus of claim 1, wherein stroke volume is determined.

8. The apparatus of claim 1, wherein breathing efficacy is determined.

9. The apparatus of claim 1, wherein said computing device calculates a heart rate and value relating to stroke volume from said heart rate and said cardiac output.

10. The apparatus of claim 1, wherein said wideband external pulse transducer comprises a foil electret transducer.

11. The apparatus of claim 1, wherein said wideband external pulse transducer comprises a piezoelectric transducer.

12. The apparatus of claim 11, wherein said wideband external pulse transducer comprises a metalized polyvinylidene fluoride polymer film.

13. The apparatus of claim 1, wherein the large arterial vascular compliance values are aortic compliance values.

14. The apparatus of claim 1 for assessing a physiological factor.

15. A method for assessing the large arterial vascular compliance of a mammal, comprising the steps of:
(a) measuring the suprasystolic waveforms of a peripheral artery with blood flow occluded;
(b) determining the difference in amplitude between a first suprasystolic peak and a first suprasystolic trough of the suprasystolic waveform;
(c) determining the difference in amplitude between a second suprasystolic peak and a second suprasystolic trough of the suprasystolic waveform;
(d) determining the ratio of a difference from step (b) to the difference from step (c); and
(e) calculating a large arterial vascular compliance value.

16. The method of claim 15, wherein the large arterial vascular compliance value is the aortic compliance value.

17. The method of claim 15, wherein in step (a) the suprasystolic waveforms are measured over a peripheral artery with a blood flow therethrough occluded.

18. The method of claim 15, further comprising the step of determining a cardiac output based upon the large arterial vascular compliance value.

19. The method of claim 15, wherein stroke volume is determined.

20. The method of claim 15, wherein cardiac output is determined.

21. The method of claim 15, wherein breathing efficacy is determined.

22. The method of claim 15, wherein patients are monitored during administration of anesthesia.

23. The method of claim 15 for better prescribing treatment for hypertension.

24. The method of claim 15, wherein shock is assessed.

25. The method of claim 15, wherein heart failure is assessed.

26. The method of claim 15 for assessing a physiological factor.

27. The method of claim 26, wherein the physiological factor is heart rate, blood pressure/pulse pressure, or pulse wave delay.

28. A noninvasive cardiac monitoring apparatus comprising:
a brachial artery cuff;
a pressure control system for controlling a pressure in said cuff;
a wideband acoustic transducer having an output and being adapted to measure acoustic emission proximate to said cuff; and
a system for analyzing said output at least during a period of complete occlusion of flow in the brachial artery due to pressurization of said cuff, to assess large arterial vascular compliance from a portion of said output representing the period of complete occlusion.

29. The apparatus of claim 28, wherein the large arterial vascular compliance is aortic compliance.

30. The apparatus of claim 28, wherein said wideband external pulse transducer comprises a foil electret transducer.

31. The apparatus of claim 28, wherein said wideband external pulse transducer comprises a piezoelectric transducer.

32. The apparatus of claim 31, wherein said wideband external pulse transducer comprises a metalized polyvinylidene fluoride polymer film.

33. The apparatus of claim 28, wherein said analyzing system comprises means for determining the difference in amplitude between a first suprasystolic peak and a first suprasystolic trough and the difference between the amplitude of a second suprasystolic peak and a second suprasystolic trough and means for calculating the ratio of the differences.

34. The apparatus of claim 28, wherein said analyzing system comprises means for determining the difference in amplitude between a first suprasystolic peak and a first suprasystolic trough and the difference between the amplitude of a third suprasystolic peak and a third suprasystolic trough and means for calculating the ratio of the differences.

35. The apparatus of claim 33 or 34, wherein said estimating means calculates said compliance value as a function of the natural logarithm of said ratio or a power function of said ratio.

36. The apparatus of claim 28, further comprising means for determining cardiac output.

37. The apparatus of claim 28 for assessing a physiological factor.

38. A method for assessing the cardiovascular status of a mammal comprising:
providing a system for locally applying a pressure to an artery, capable of restricting blood flow through said artery;
providing a wideband external pulse transducer having an output and situated to measure acoustic suprasystolic signals proximate to said artery; and
analyzing the output of the wideband external pulse transducer to calculate a large arterial vascular compliance value based on the suprasystolic signals.

39. The method of claim 38, wherein the large arterial vascular compliance value is an aortic compliance value.

40. The method of claim 38, wherein said analysis determines a likely diagnosis or prognosis of the mammal.

41. The method of claim 38 which assesses whether a pregnant mammal has a preeclampsia condition.

42. The method of claim 38 which assesses whether the mammal has cardiac insufficiency.

43. The method of claim 38, wherein breathing efficacy is determined.

44. The method of claim 38, wherein cardiac arrhythmias are assessed.

45. The method of claim 38, wherein endothelia dysfunction is assessed.

46. The method of claim 38, wherein a cardiovascular aging profile is determined.

47. The method of claim 38, wherein the diastolic reflective wave assesses the degree of peripheral vasoconstriction.

48. The method of claim 38, wherein suprasystolic signals are used to measure the duration of systole and/or the duration of diastole.

49. The method of claim 38, wherein patients are monitored during administration of anesthesia.

50. The method of claim 38 for better prescribing treatment for hypertension.

51. The method of claim 38, wherein shock is assessed.

52. The method of claim 38, wherein heart failure is assessed.

53. The method of claim 38 for assessing a physiological factor.

54. The method of claim 53, wherein the physiological factor is heart rate, blood pressure/pulse pressure, or pulse wave delay.

* * * * *